(12) United States Patent
Ninomiya et al.

(10) Patent No.: US 8,627,531 B2
(45) Date of Patent: **\*Jan. 14, 2014**

(54) VACUUM CLEANER AND DEVICE HAVING ION GENERATOR

(75) Inventors: Kohji Ninomiya, Nara (JP); Mikio Yagi, Osaka (JP); Shigenori Hato, Osaka (JP); Kazumasa Hayashi, Osaka (JP); Hiroshi Yoshimura, Osaka (JP); Yoshihiro Shimizu, Osaka (JP); Hideo Nojima, Nara (JP); Hisaharu Yagi, Nara (JP); Kazuo Nishikawa, Osaka (JP); Tetsuyuki Ohtani, Nara (JP)

(73) Assignee: Sharp Kabushiki Kaisha, Osaka (JP)

( \* ) Notice: Subject to any disclaimer, the term of this patent is extended or adjusted under 35 U.S.C. 154(b) by 808 days.

This patent is subject to a terminal disclaimer.

(21) Appl. No.: 12/436,872

(22) Filed: May 7, 2009

(65) Prior Publication Data

US 2009/0211052 A1    Aug. 27, 2009

Related U.S. Application Data

(63) Continuation of application No. 10/487,603, filed as application No. PCT/JP02/08900 on Sep. 2, 2002, now Pat. No. 7,591,043.

(30) Foreign Application Priority Data

Sep. 4, 2001 (JP) ................................. 2001-266692
Mar. 8, 2002 (JP) .................................. 2002-63629

(51) Int. Cl.
*A47L 9/10* (2006.01)

(52) U.S. Cl.
USPC .................................. 15/1.51; 15/339; 15/414

(58) Field of Classification Search
USPC .......................... 15/339, 315, 331, 415, 1.51
See application file for complete search history.

(56) References Cited

U.S. PATENT DOCUMENTS

| 4,849,628 A | 7/1989 | McLuckey et al. |
| 5,072,243 A | 12/1991 | Casey |
| 5,185,903 A | 2/1993 | Choi |

(Continued)

FOREIGN PATENT DOCUMENTS

| DE | 38 20 931 A1 | 12/1989 |
| DE | 199 33 180 A1 | 1/2001 |

(Continued)

OTHER PUBLICATIONS

European Search Report for corresponding Application No. 02772829.4 dated Aug. 3, 2005.

*Primary Examiner* — Lee D Wilson
(74) *Attorney, Agent, or Firm* — Renner, Otto, Boisselle & Sklar, LLP

(57) ABSTRACT

When the electrically driven fan (14) of a vacuum cleaner is driven, air containing dust is drawn into the cleaner main body (1) through a hose (7) connected to a hose socket (8) and is exhausted into the outside of the cleaner main body (1) through an exhaust port (1b) via first and second suction passageways (10, 13). Disposed outside the first suction passageway (10) is an ion generator (23), it being arranged that plus and minus ions generated in the ion generator (23) are fed to the air stream flowing in the first suction passageway (10). Since the plus and minus ions kill floating germs in the air stream, the exhaust can be purified.

11 Claims, 23 Drawing Sheets

(56) References Cited

U.S. PATENT DOCUMENTS

| | | |
|---|---|---|
| 5,351,354 A | 10/1994 | Hasumi et al. |
| 5,920,954 A * | 7/1999 | Sepponen ............... 15/339 |
| 6,199,244 B1 * | 3/2001 | Hilgers et al. ............ 15/339 |
| 7,040,101 B2 * | 5/2006 | Takeda et al. ............... 62/78 |
| 7,174,593 B2 | 2/2007 | Soejima et al. |
| 7,257,852 B2 * | 8/2007 | Shibuya et al. ............ 15/1.51 |
| 7,591,043 B2 * | 9/2009 | Ninomiya et al. ......... 15/339 |
| 2001/0027087 A1 | 10/2001 | Shiomi et al. |
| 2005/0000054 A1 * | 1/2005 | Ninomiya et al. ......... 15/347 |
| 2009/0211052 A1 * | 8/2009 | Ninomiya et al. ......... 15/339 |

FOREIGN PATENT DOCUMENTS

| | | |
|---|---|---|
| FR | 2 490 110 A | 3/1982 |
| GB | 1 025 064 A | 4/1966 |
| GB | 1 501 927 A | 2/1978 |
| JP | 61-170451 | 10/1986 |
| JP | 64-027156 | 1/1989 |
| JP | 2-29648 | 2/1990 |
| JP | 3-133416 | 6/1991 |
| JP | 03-162814 | 7/1991 |
| JP | 5-253148 | 10/1993 |
| JP | 6-315447 | 11/1994 |
| JP | 7-327873 | 12/1995 |
| JP | 2001-079446 | 3/2001 |
| JP | 2001-218708 | 8/2001 |

* cited by examiner

VACUUM CLEANER AND DEVICE HAVING ION GENERATOR

CROSS REFERENCE TO RELATED APPLICATION

This application is a continuation of U.S. patent application Ser. No. 10/487,603 filed Feb. 23, 2004, which is a 371 of PCT/JP02/08900, filed on Sep. 2, 2002, which is hereby incorporated herein by reference in its entirety.

TECHNICAL FIELD

The present invention relates to an electric vacuum cleaner, and more particularly to an electric vacuum cleaner provided with a sterilizing function.

BACKGROUND ART

As a conventional electric vacuum cleaner provided with an ozone generating function, the one disclosed in Japanese Patent Application Laid-Open No. H1-238815 will be described below with reference to FIG. 30. In this conventional electric vacuum cleaner, inside a body 101 thereof is formed a suction air passage 104 that runs from a hose socket 102 formed in the front wall of the body 101 to an exhaust opening 103 formed in the rear wall of the body 101, and in this suction air passage 104 are arranged a dust collection bag 105, a dust filter 106, and an electric blower 107 in this order. The dust collection bag 105 permits air to pass therethrough. The electric blower 107 communicates with the exhaust opening 103.

When the electric blower 107 is driven, air containing dust is sucked in through a suction hose 108 fitted into the hose socket 102, is then passed through the dust collection bag 105, dust filter 106, and electric blower 107, and is then discharged out of the body 101 through the exhaust opening 103. Meanwhile, the dust collection bag 105 removes the dust contained in the air.

On the other hand, inside the body 101 of this electric vacuum cleaner, outside and above the suction air passage 104 is formed an ozone reservoir 109, in which an ozone generator 110 is provided. While the electric blower 107 is operating, ozone generated by the ozone generator 110 is reserved in the ozone reservoir 109, and, when the electric blower 107 is de-energized, valves 111 and 112 are opened so that the reserved ozone is fed into the suction air passage 104 so as to kill germs present in the suction air passage 104.

In this conventional electric vacuum cleaner, the ozone fed into the suction air passage 104 acts on the stream of air that has been cleaned by the dust collection bag 105, but does not sufficiently act on the dust and germs collected in the dust collection bag 105. This makes it impossible for ozone to exert a satisfactory antibacterial effect.

Moreover, since ozone is reserved in the ozone reservoir 109 during operation, the body 101, which is formed of synthetic resin, is exposed to the reserved ozone for a long time. This causes the body 101 to deteriorate, making it prone to cracks and breakage in the relevant part thereof. In particular, in a vacuum-type cleaner, cracks are likely to develop in a part thereof where the pressure is low during operation, lowering the suction performance and leading ultimately to a burst.

DISCLOSURE OF THE INVENTION

The present invention has been devised to address the aforementioned problems with conventional electric vacuum cleaners. Specifically, according to the present invention, an electric vacuum cleaner that, while driving an electric blower, sucks in air containing dust such as dirt, particulate dust, and water, then passes the air through a suction air passage, and then discharges the air out of itself is provided with an ion generator. The ion generator generates $H^+(H_2O)_n$ as positive ions and $O_2^-(H_2O)_m$ as negative ions, which are fed into the suction air passage. In this construction, the positive and negative ions generated by the ion generator are discharged into the suction air passage so as to sterilize the stream of air, exerting a satisfactory antibacterial effect. The ion generator may be disposed outside the suction air passage, with the ions fed into the suction air passage. The positive and negative ions generated by the ion generator may be fed into the air on the downstream side of the electric blower where the air is about to be discharged.

Incidentally, as the ion generator generates positive and negative ions, it also generates ozone as a byproduct. Accordingly, by treating the part of the suction air passage around the needle-shaped electrode with anti-ozone treatment, it is possible to prevent its deterioration caused by ozone. As is well known, as temperature rises, ozone exerts increasingly high oxidizing power, prompting the deterioration of the components arranged nearby, especially those formed of resin materials. For this reason, to reduce the oxidizing power of the ozone present around the electrode, i.e., the source at which ozone is generated, it is ideal to place the ion generator away from a heat source such as the electric blower.

By passing the air sucked into the electric vacuum cleaner through an purification filter before discharging it out of the electric vacuum cleaner, and by mixing the air that has been passed through the purification filter with the positive and negative ions, it is possible to kill germs that have passed through the purification filter without being caught by it.

Alternatively, according to the present invention, an electric vacuum cleaner that has casters arranged on both side faces of a body having an electric blower housed therein and that exhausts the electric blower of air through ventilation openings formed in the casters is provided with an ion generator that generates $H^+(H_2O)_n$ as positive ions and $O_2^-(H_2O)_m$ as negative ions into a mixing chamber formed by the casters. In this construction, positive and negative ions are generated by the ion generator inside the mixing chamber formed by the casters, and the positive and negative ions are then discharged, by being carried by the stream of air passing through the electric vacuum cleaner, through the ventilation openings formed in the casters to sterilize the interior of the room. This is expected to produce a satisfactory antibacterial effect.

Alternatively, an electric vacuum cleaner has an electric blower and an ion generator housed in a body, and the body is provided with, independently of a control panel for controlling the electric vacuum cleaner, a drive switch for driving the ion generator. With this construction, for example, when only the body of the electric vacuum cleaner, i.e., with its hose removed, is placed inside a closet or the like, and the drive switch is turned on to suck in and discharge the air inside the space such as a closet, it is possible to discharge the generated positive and negative ions into the space and thereby achieve purification in the space.

In this case, it is preferable to provide timer means for driving the electric blower and the ion generator for a predetermined length of time after the drive switch is operated.

The quantities of ions generated by the ion generator may be controlled according to the power with which the electric blower is driven. This prevents unnecessary operation of the ion generator, and thus helps extend its life. Moreover, it is possible to prevent unnecessary discharge of ions.

The ion generator may be driven for a predetermined length of time according to the storage state of the electric vacuum cleaner. This permits purification to be performed automatically for a predetermined length of time inside a comparatively airtight space such as the storage space during storage.

If both positive and negative ions are generated with a single ion generating electrode, part of them cancel each other, resulting in lower effective quantities of ions generated at the initial stage of generation. To avoid this, it is preferable to provide two electrodes so that positive and negative ions are generated from separate electrodes.

This makes it possible to variably control the proportion between the quantities of positive and negative ions generated.

Incidentally, the aforementioned ion generator is of the type that generates both positive and negative ions or negative ions alone. It is believed that positive and negative ions exert an effect of killing germs floating in the air, and that negative ions exert an effect of relaxing the feelings of humans.

It is particularly preferable to design and operate the ion generator in such a way that, when air is fed to the ion generating part thereof at the rate of 50 cm/s or more, the concentrations of positive and negative ions are each 10,000 ions/cm$^3$ or more at a position 10 cm away from the ion generating part. This helps obtain a high sterilizing effect.

Here, only such examples are dealt with in which an electric vacuum cleaner is provided with an ion generator. It is, however, also possible to provide an ion generator for generating ions in any device that is furnished with an air blowing means and a moving means, such as wheels, so that it can be moved around while in use, for example a mobile cleaning robot. This permits the ion generator to be moved around while in operation, and thus makes it possible to purify air efficiently and unattendedly over a wide area or behind an obstacle where a stationary ion generator cannot reach. Thus, it is possible to purify air wherever such a device can be brought into without performing cleaning by suction.

BEST MODE FOR CARRYING OUT THE INVENTION

Hereinafter, embodiments of the present invention will be described in detail with reference to the drawings. The examples described hereinafter all deal with a so-called cyclone-type electric vacuum cleaner, in which air containing dust and the like is sucked into a cylindrical dust collection case and is passed through a circular suction air passage in such a way that the air swirls around inside the cylinder of the dust collection case so that, by the action of centrifugal force, the dust and the like contained in the air is separated therefrom and collected.

Figure 1:
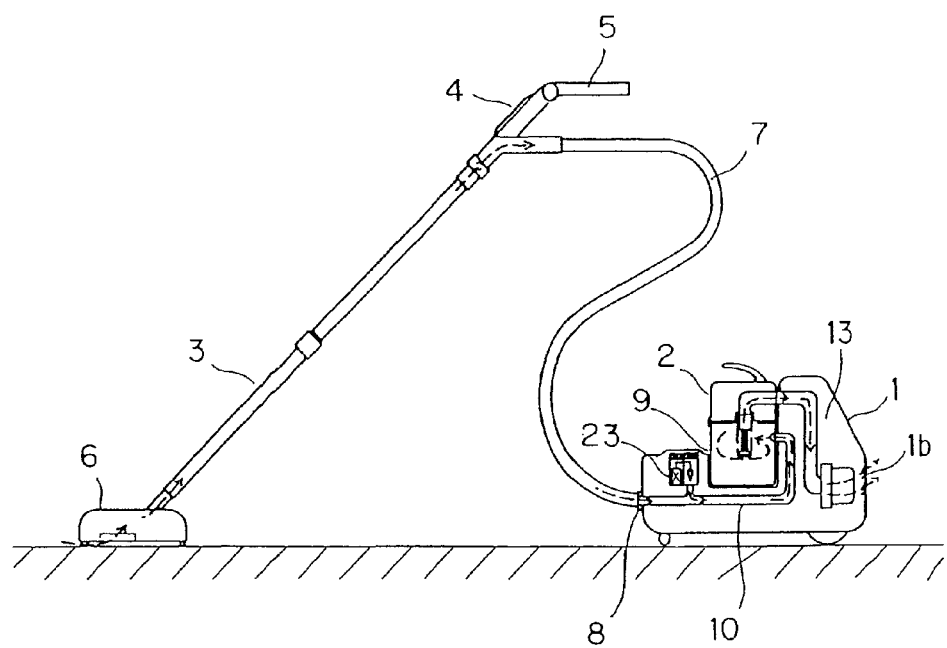
FIG. 1 is an external side view showing the electric vacuum cleaner of a first embodiment of the invention.
Figure 2:
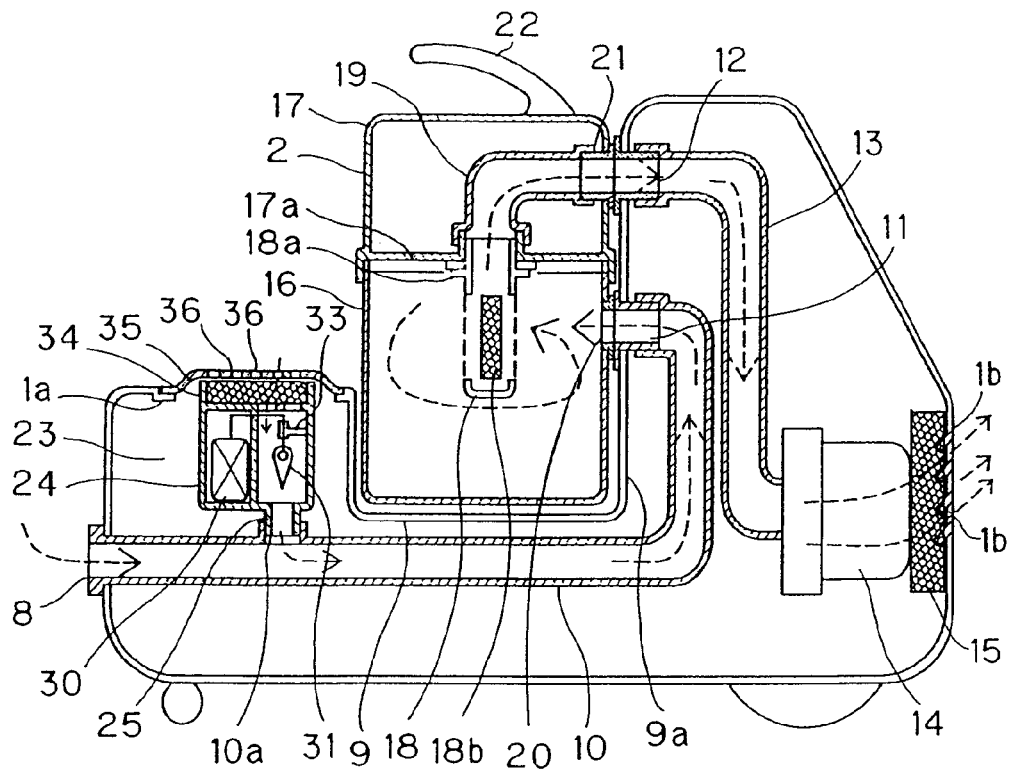
FIG. 2 is a side sectional view showing the internal construction of the body of the electric vacuum cleaner.

A first embodiment of the invention will be described below with reference to the drawings. FIG. 1 is an external view showing the outward appearance of the cyclone-type electric vacuum cleaner of a first embodiment of the invention, and FIG. 2 is a side sectional view of its body. As will be clear from these figures, the electric vacuum cleaner is roughly divided into the following parts: an electric vacuum cleaner body (hereinafter, simply the "body") 1; a dust collector 2 that is removably attached to the body 1; a connection pipe 3 that has a control panel 4 and a handle 5 provided at the upper end thereof and that has a nozzle unit 6 removably attached to the lower end thereof, and a connection hose 7 of which one end is removably connected to the connection pipe 3 and of which the other end is removably fitted into a hose socket 8 formed as an air intake opening in the body 1.

As shown in FIG. 2, the body 1 is built as a casing of which the contour as seen from the side is substantially L-shaped so as to form, in a central part in the top face thereof, a housing 9 for removably supporting the dust collector 2. Inside the body 1 are provided the following parts: a first suction air passage 10 that starts from the hose socket 8, which is formed in the front wall of the body 1, then extends horizontally inside the body 1, then bends upward, and then connects to a first coupling member 11 provided on a horizontal wall surface 9a of the housing 9; a second suction air passage 13 that is, at one end thereof, connected to a second coupling member 12 provided on the horizontal wall surface 9a at a level higher than the first coupling member 11 and that then bends downward so that the other end thereof extends toward an exhaust opening 1b formed in the rear wall of the body 1; an electric blower 14 that is connected to the other end of the second suction air passage 13; and a deodorizing filter 15 that is disposed between the electric blower 14 and the exhaust opening 1b.

As shown in FIG. 2, the dust collector 2 is composed of the following parts: a dust cup 16 built as a cylindrical container that is open at the top and that has an inflow pipe 20 fitted into the side wall thereof, a lid 17 that is fitted on the dust cup 16 so as to close the top opening thereof, an exhaust cylinder 18 that is fitted in a central part of a separator plate 17a provided in the lid 17 so as to suspend therefrom into the dust cup 16; and an exhaust pipe 19 that is housed inside the lid 17 and that is connected, at one end thereof, to an exhaust port 18a of the exhaust cylinder 18 and, at the other end thereof, to an outflow pipe 21 fitted into the side wall of the lid 17.

A filter 18b is arranged in the outer circumferential wall of the exhaust cylinder 18. The dust collector 2 is removably housed in the housing 9 of the body 1, and, when it is housed in position, the inflow pipe 20 and outflow pipe 21 communicate with the first coupling member 11 and second coupling member 12, respectively. Here, the first coupling member 11 and second coupling member 12 are both formed of elastic material such as rubber so that, in particular by flange-like parts formed at one end thereof, their communication with the inflow pipe 20 and outflow pipe 21 is kept air-tight when the dust collector 2 is housed in the housing 9.

A handle 22 is fitted on the top surface of the lid 17 of the dust collector 2. An ion generator 23 is disposed near the hose socket 8, on the inner surface side of the top wall of the body 1. The ion generator 23 discharges ions from an electrode by applying a voltage to the electrode. Here, by switching the type (negative or positive) of the voltage with which the electrode is loaded, it is possible to switch the generated and thus discharged ions between positive and negative ions.

By providing a selecting means for switching, continuously or at predetermined time intervals, the type of the voltage with which the electrode is loaded, it is possible to easily choose between positive and negative ions. Negative ions exert a healing effect, and discharging positive and negative ions simultaneously produces a sterilizing effect. The ion generator 23 may be configured in any manner, so long as it is designed as a device provided with a means for generating ions. In the following descriptions, the healing, sterilizing, and other effects brought about by ions are collectively referred to as "purification."

Figure 3:
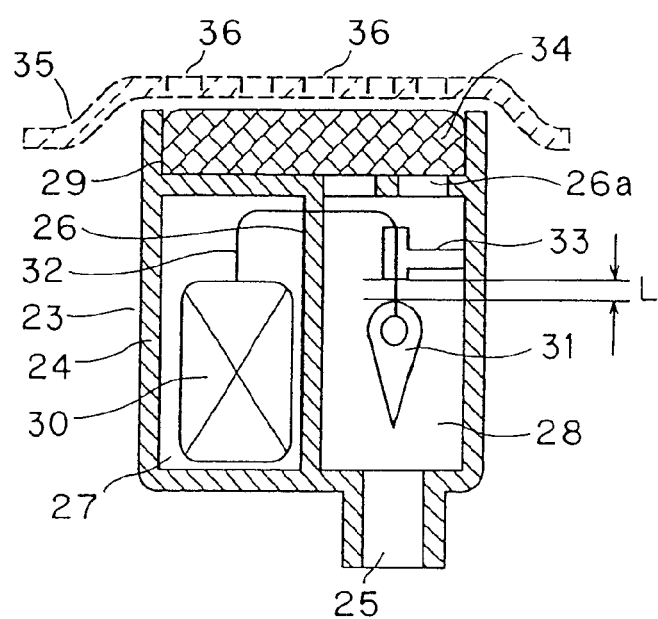
FIG. 3 is an enlarged side sectional view showing the internal construction of the ion generator used in the electric vacuum cleaner.

Now, the ion generator 23 will be described, assuming that it has a needle-shaped electrode. A practical example of the details of the ion generator 23 is shown in FIG. 3. As shown in this figure, the ion generator 23 has a body casing 24, which has an ion outflow port 25 formed in the bottom face thereof and of which the interior is divided into a front chamber 27, a rear chamber 28, and an upper chamber 29. The front chamber 27 is located in front of the rear chamber 28, with the two chambers separated from each other by a separation wall 26. The upper chamber 29 is located above the front and rear chamber 27 and 28, and communicates only with the rear chamber 28 through a communication port 26a.

In the front chamber 27 is arranged an ion generating circuit 30. On the other hand, in the rear chamber 28, which serves as an ion generation chamber, is arranged a needle-shaped electrode 31, which has its tip end shaped into a needle pointing toward the ion outflow port 25 and which serves as an ion generating element. A conductor lead 32, which is formed of a single wire, runs from the ion generating circuit 30, then penetrates the separation wall 26, and then further runs inside the rear chamber 28, where the conductor lead 32 is supported by a supporting member 33 formed of insulating material such as synthetic resin and provided on the wall. Below the supporting member 33, the conductor lead 32 connects, both electrically and mechanically, to the needle-shaped electrode 31, with the needle-shaped end thereof pointing downward.

Thus, supported by the supporting member 33 at its top, the needle-shaped electrode 31 is stably kept in position. In a case where the conductor lead 32 is formed of twisted wires, the needle-shaped electrode 31 may be supported directly by the supporting member 33. A filter 34 is arranged in the upper chamber 29.

The ion generator 23 configured as described above is disposed near the hose socket 8, on the inner surface side of the top wall of the body 1, with the ion outflow port 25 connected to a connection port 10a formed in the middle of the first suction air passage 10. The filter 34 arranged inside the upper chamber 29 faces a number of air intake holes 36 formed in the top wall of the body 1. More precisely, these air intake holes 36 are formed all over a reversed-dish-shaped cover 35 that closes an opening 1a formed in the top wall of the body 1 and thereby covers the filter 34 arranged in the upper chamber 29.

In FIG. 2, the deodorizing filter 15 located on the downwind side of the needle-shaped electrode 31 is composed of a corrugated-honeycomb-shaped member coated with a low-temperature deodorant catalyst and an absorbent. This deodorizing filter 15 is removably disposed between the electric blower 14 and the exhaust opening 1b so that it can be replaced and cleaned to keep the interior of the electric vacuum cleaner clean. The deodorizing filter 15 may be composed of a filter or a piece of unwoven fabric impregnated with a low-temperature deodorant catalyst and an absorbent, but a honeycomb-shaped structure is preferable because it minimizes the pressure loss. The deodorizing filter 15 may be treated with antibacterial treatment.

The low-temperature deodorant catalyst is a copper-manganese-based oxide that oxidizes and thereby decomposes order-producing substances such as amine- and thiol-based volatile substances and hydrogen sulfide. A copper-manganese-based oxide also functions as an ozone-decomposing catalyst, and thus helps decompose ozone. This eliminates the need to separately provide an ozone eliminating device, and thus helps minimize the increase in the manufacturing costs of the electric vacuum cleaner. Moreover, it is possible to reduce the ozone concentration to so low a level as to be negligible in terms of the deterioration of resin-molded components.

Thus, the ozone contained in the air sucked in is decomposed by the deodorizing filter 15 provided in the body 1, and is therefore not discharged out of the body 1. The deodorizing filter 15 may be impregnated with a dedicated ozone-decomposing catalyst that effectively decomposes ozone. Examples of such ozone-decomposing catalysts include, to name a few, manganese dioxide, platinum powder, lead dioxide, copper oxide II, and nickel.

The deodorizing filter 15 may be provided with a HEPA filter or a sterilizing filter impregnated with a germicide. This helps further enhance the sterilizing, antibacterial, and dust-removing effects. The deodorizing filter 15 may be impregnated with an absorbent. This absorbent is for absorbing odor-producing substances, ozone, and airborne germs. Examples of such absorbents include, to name a few, silica gel, activated charcoal, zeolite, and sepiolite. The deodorizing filter 15 may be separately provided with a granulate or particulate absorbent.

The electric vacuum cleaner according to the invention is constructed as described above, and operates as described below. When the control panel 4 is so operated as to start operation, the electric blower 14 and the ion generating circuit 30 are energized, so that the electric blower 14 starts to be driven to suck air in through the nozzle unit 6 and the ion generating circuit 30 starts to operate to apply a high voltage to the needle-shaped electrode 31. As a result, first, as the electric blower 14 is driven, as indicated by broken-line arrows in FIG. 1, the air, containing dust, sucked in through the nozzle unit 6 is introduced, through the connection pipe 3, connection hose 7, and hose socket 8, into the body 1.

As air is sucked in this way, inside the body 1, as indicated by broken-line arrows in FIG. 1, the stream of air passing through the first suction air passage 10 produces a negative pressure near the connection port 10a and the ion outflow port 25, and thus the air in the rear chamber 28, which serves as the ion generation chamber of the ion generator 23, is sucked into the first suction air passage 10. As a result, air is sucked in through the air intake holes 36 from outside, is then passed through the filter 34, and is then, along with the ions generated in the rear chamber 28, sucked into the first suction air passage 10.

A blower (for example, like the blower 23a shown in FIG. 13) may be additionally provided to blow out the generated ions through the ion outflow port 25 of the ion generator 23. This permits ions to be fed effectively into the first suction air passage 10. Moreover, ions can then be discharged irrespective of whether the electric blower 14 is being driven or not. This makes it possible to discharge ions to purify air even when the electric blower 14 is not operating.

This air containing ions is, along with the stream of air sucked through the hose socket 8 into the first suction air passage 10, sucked through the first coupling member 11 and the inflow pipe 20 into the dust cup 16 while swirling around. Thus, the stream of air swirls around inside the dust cup 16, with the result that, by the action of centrifugal force, the dust contained in the stream of air is separated from the air and is collected inside the dust cup 16.

On the other hand, the air having dust removed therefrom and thus purified is sucked through the filter 18b into the exhaust cylinder 18, is then passed through the exhaust pipe 19, outflow pipe 21, and second coupling member 12 into the second suction air passage 13, and is then passed through the electric blower 14 and deodorizing filter 15 so as to be discharged out of the body 1 through the exhaust opening 1b. Meanwhile, various germs present in the stream of air are killed by the ions generated by the needle-shaped electrode 31, with the result that the air is purified.

The present invention works as described above, and the ion generator 23 mentioned above works as described below. When a high voltage is applied from the ion generating circuit 30 by way of the conductor lead 32 to the needle-shaped electrode 31, an electric field concentrates on the point of the needle-shaped electrode 31. Thus, when the air taken in through the air intake holes 36 reaches around the needle-shaped electrode 31, insulation in the air is destroyed locally at the point of the needle-shaped electrode 31, causing corona discharge.

The corona discharge here produces positive and negative ions, which flock together and surround airborne germs floating in the air and kill them by the action of active species such as hydroxyl radical .OH and hydrogen peroxide $H_2O_2$. Thereafter, the deodorizing filter 15 absorbs and thereby eliminates the odor-producing substances originating from the dust and the like collected in the dust cup 16 and elsewhere and the minute quantity of ozone produced by the corona discharge. When the motor 54 of the electric blower 14 is not operating, positive and negative ions may be fed directly to the dust cup 16 to fill it with the ions so as to enhance the sterilizing effect inside the dust cup 16.

In this embodiment, the conductor lead 32 is given a length of 200 mm or less to reduce the lowering of discharge efficiency and to permit easy wiring. Preferably, the conductor lead 32 is given a length of 100 mm or less to further reduce the lowering of discharge efficiency; more preferably, it is given a length of 50 mm or less to permit connection of the needle-shaped electrode 31 with almost no lowering of discharge efficiency.

As the result of the corona discharge at the needle-shaped electrode 31, when the voltage applied thereto is positive, positive ions, mainly $H^+(H_2O)_n$, are generated; when the voltage is negative, negative ions, mainly $O_2^-(H_2O)_m$, are generated. These positive and negative ions, namely $H^+(H_2O)_n$ and $O_2^-(H_2O)_m$, flock together on the surface of microorganisms, and surround airborne germs such as microorganisms present in the air.

Then, as expressed by the formulae noted below, they collide together to produce active species, namely hydroxyl radical .OH and hydrogen peroxide $H_2O_2$, on the surface of microorganisms and the like and thereby kill airborne germs. In this way, in this embodiment, airborne germs present in the air are killed by the action of positive and negative ions. This makes it possible to obtain a more efficient sterilizing effect than with conventional methods of sterilization exploiting the action of ozone.

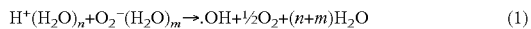  (1)

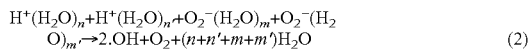  (2)

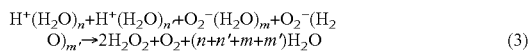  (3)

Moreover, there is provided no opposing electrode opposite the needle-shaped electrode 31, or no collecting electrode for collecting positive ions. Thus, no ions are absorbed by such electrodes due to a voltage difference. This permits ions to be spread widely inside the rear chamber 28, i.e., the ion generation chamber, even without a strong blow of air. Accordingly, the ions spread in the rear chamber 28 are then efficiently sucked through the connection port 10*a* and the ion outflow port 25 into the first suction air passage 10. This helps enhance the sterilizing power.

Moreover, both a positive and a negative voltage are applied to the needle-shaped electrode 31, and therefore the ion generating circuit 30 never remains charged even without being grounded. This eliminates the need to secure a ground to the earth, and thus permits the electric vacuum cleaner to be moved freely around.

According to formulae (1) to (3) noted above, to produce the active species, the quantity of negative ions generated needs to be equal to or larger than the quantity of positive ions generated. In this embodiment, the quantity of positive ions generated is made smaller than that of negative ions. This permits positive and negative ions to flock together on the surface of microorganism and produce active species to kill airborne germs, and simultaneously permits the extra negative ions to suppress the proliferation of airborne germs.

Here, if the quantity of positive ions generated is less than 3% of the quantity of negative ions generated, .OH is produced in too small a quantity to obtain satisfactory sterilizing power. For this reason, in this embodiment, where sterilization is aimed at, the quantity of positive ions generated is made 3% or more of the quantity of negative ions generated. Moreover, by making the quantity of positive ions generated equal to or more than 5,000 ions (preferably, 10,000 ions) per 1 cm$^3$, it is possible to obtain sufficient sterilizing power. Moreover, by providing control that permits the proportions of positive and negative ions generated to be varied, it is possible to generate appropriate quantities of positive and negative ions according to whether the desired effect is a sterilizing, healing, or other effect.

Two ways of controlling the quantities of ions generated are:

(1) to vary the durations for which a positive and a negative voltage are applied respectively; and (2) to control the duty of voltage application, i.e., the durations for which a voltage is and is not applied.

Moreover, the voltage applied to the needle-shaped electrode 31 is made so low as to minimize the quantity of ozone produced by corona discharge. In addition, when the duty is controlled, it is preferable to turn on and off the applied voltage repeatedly at short time intervals, because this helps reduce the generation of ozone. As temperature rises, ozone exerts increasingly high oxidizing power, prompting the deterioration of the components arranged nearby, especially those formed of resin materials.

Figure 4:
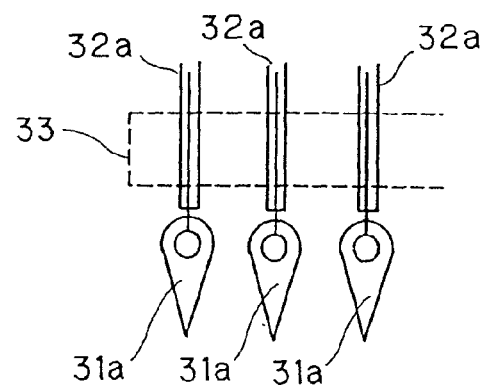
FIG. 4 is an enlarged view of another example of the needle-shaped electrode of the ion generator.

To cope with this problem, in this embodiment, the needle-shaped electrode 31 is disposed in an upstream part of the stream of air so as not to be affected by the heat generated by the electric blower 14, i.e., inside the rear chamber 28, which is located away from a heat source such as the electric blower 14. As a result, even when ozone is generated, its oxidizing power around the needle-shaped electrode 31, i.e., the source at which it is generated, is minimized. As shown in FIG. 4, the needle-shaped electrode 31 may be composed of a plurality of needle-shaped conductors 31*a* that are kept at an equal potential and that are supported by a common supporting member 33 via conductor leads 32*a*.

Figure 5:
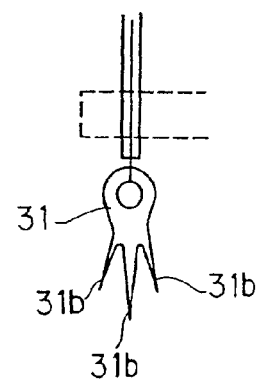
FIG. 5 is an enlarged view of still another example of the needle-shaped electrode of the ion generator.

Alternatively, as shown in FIG. 5, a plurality of needle-shaped parts 31*b*, for example three of them, may be formed at the lower end of a single needle-shaped electrode 31. In this case, ions are discharged from the ends of the needle-shaped parts 31*b* into a range of angles covering about 45°. In this way, by arranging a plurality of needle-shaped parts 31*b* so that they point in different directions, it is possible to discharge ions into a wide range and thereby obtain enhanced purifying power.

The direction in which the needle-shaped electrode 31 causes discharge is set to be along the direction of the stream of air. This permits ions to be discharged over a wider area in the direction of the stream of air. This also makes dust less likely to settle on the needle-shaped electrode 31, permitting easy maintenance.

Part of the wall of the suction air passage, especially the part thereof located on the downstream side of the ion generator 23, may be treated with anti-ozone treatment as by being coated with a metal, or being coated with an ozone-resistant substance, or being covered with a metal sheet. This helps confine most of the generated ozone inside the wall of the suction air passage, and thus helps alleviate the deterioration of the components arranged nearby other than the wall of the suction air passage.

If the distance (L in FIG. 3) between the supporting member 33 and the needle-shaped electrode 31 is too short, when the humidity in the room where cleaning is performed is high, a high voltage may be applied to the supporting member 33. To avoid this, the distance L is set to be 3.5 mm or more, for example 5 mm, so that the supporting member 33 is located away from the needle-shaped electrode 31 and is thereby surely insulated therefrom. This permits the high voltage to be stably applied to the needle-shaped electrode 31, permits corona discharge to take place surely, and thus permits ions to be discharged stably.

When both positive and negative ions are generated with a single needle-shaped electrode 31, part of them cancel each other, resulting in lower effective quantities of ions generated at the initial stage of generation. This problem can be overcome by providing two electrodes so that positive and negative ions are generated separately. This helps increase the effective quantities of ions generated.

Moreover, this construction permits the two electrodes to be controlled independently, and thus permits easy and separate adjustment of the quantities of positive and negative ions. Needles to say, even when two electrodes are provided in this way, it is possible to drive only one of them to generate ions of one type alone.

As the circuit configuration, applied voltage, electrode shape, electrode material, and other factors are varied, the two electrodes, for example a plurality of electrodes consisting of two types of electrodes, permit easy adjustment of the balance with which ions are generated. Moreover, by arranging the two electrodes 10 mm or more, for example 30 mm, apart from each other, it is possible to use the generated ions effectively for sterilization with almost no cancellation between positive and negative ions.

The two electrodes may be given any other shape than a needle-like one. For example, ions may be generated with a voltage applied between electrodes that are arranged so as to face each other with an insulator sandwiched in between. By arranging a plurality of electrodes at predetermined intervals (for example, 10 mm) in a direction approximately perpendicular to the direction of the stream of air, and arranging the electrodes, especially when there are provided three or more of them, in such a way that they are inclined alternately in opposite directions, and arranging every two adjacent electrodes, which are inclined in opposite directions, at predetermined angles such that their points tend to overlap, i.e., make contact with, each other in the direction of the stream of air (for example, at angles of about 30° in such directions in which they come closer together toward the stream of air). This permits ions to be generated and distributed more evenly over a wider area, and thus helps further enhance the sterilizing power.

In this case also, as described above, by generating positive and negative ions alternately, or by generating positive and negative ions with separate electrodes, it is possible to efficiently and evenly generate and distribute ions over a wide area, and thereby further enhance the sterilizing power.

The ion generator 23 is driven with one of the following patterns of timing:

(1) The ion generator 23 is turned on and off completely in synchronism with the timing with which the power switch of the electric blower 14 is turned on and off. This permits the ion generator 23 to be turned on and off as the user wishes it to be, and thus contributes to safety.

(2) The ion generator 23 is turned off with a delay after the power switch of the electric blower 14 is turned off. This permits sterilization of the air that has just been exhausted and is still floating around.

(3) The ion generator 23 is turned on and off independently of the turning on and off of the power switch of the electric blower 14. This permits the ion generator 23 to be turned on to purify air even during storage, and thus makes it possible to purify the air inside the storage space, for example a closet, during storage.

(4) The quantities of ions generated are controlled in a manner interlocked with the control of the power with which the electric blower 14 is driven. This prevents unnecessary operation of the ion generator 23, and thus helps extend its life. Moreover, it is possible to prevent unnecessary discharge of ions.

Figure 6:
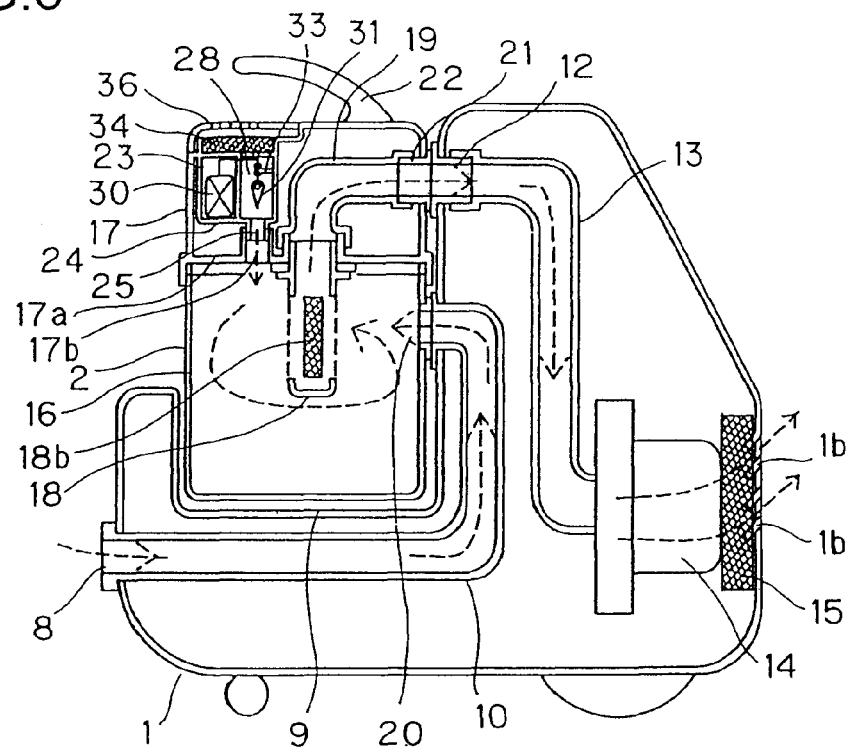
FIG. 6 is a side sectional view showing the internal construction of the electric vacuum cleaner of a second embodiment of the invention.

A second embodiment of the invention will be described below with reference to the drawings. FIG. 6 is a diagram showing the second embodiment of the invention. In this embodiment, an ion generator 23 is coupled to the inner wall surface of the ceiling of the lid of the dust collector 2. The ion outflow port 25 formed in the bottom face of the body casing 24 communicates with an opening 17b formed in the separator plate 17 of the lid 17, and outside air is taken in through air intake holes 36 formed in the ceiling wall of the lid 17.

In this construction, when the control panel 4 is so operated as to start operation, the electric blower 14 and the ion generating circuit 30 are energized, so that the electric blower 14 starts to be driven to suck air in through the nozzle unit 6 and the ion generating circuit 30 starts to operate to apply a high voltage to the needle-shaped electrode 31.

As a result, first, as the electric blower 14 is driven, the air, containing dust, sucked in through the nozzle unit 6 is introduced, through the hose socket 8, into the body 1. As air is sucked in this way, inside the body 1, as indicated by broken-line arrows in FIG. 6, the air sucked into the suction air passage 10 is sucked through the inflow pipe 20 into the dust cup 16 of the dust collector 2 while swirling around.

Thus, the stream of air swirls around inside the dust cup 16, with the result that, by the action of centrifugal force, the dust contained in the stream of air is separated from the air and is collected inside the dust cup 16. The air having dust removed therefrom and thus purified is sucked through the filter 18b into the exhaust cylinder 18, is then passed through the exhaust pipe 19, outflow pipe 21, and second coupling member 12 into the second suction air passage 13, and is then passed through the electric blower 14 and deodorizing filter 15 so as to be discharged out of the body 1 through the exhaust opening 1b.

On the other hand, as indicated by broken-like arrows in FIG. 6, the air swirling around inside the dust cup 16 produces a negative pressure near the ion outflow port 25, and thus the air in the rear chamber 28 is sucked into the dust cup 16. As a result, the air sucked in through the air intake holes 36 from outside is passed through the filter 34, is then, along with the ions generated in the rear chamber 28, sucked into the dust cup 16, is then, along with the stream of air swirling inside the dust cup 16, into the second suction air passage 13, and is then passed through the electric blower 14 and the deodorizing filter 15 so as to be discharged out of the body 1 through the dust cup 16. Meanwhile, various germs present in the stream of air are killed by the ions generated by the needle-shaped electrode 31, with the result that the air is purified.

In this embodiment, as described above, the ion generator 23 is disposed inside the dust collector 2 and outside the suction air passage, and the ions generated by the ion generator 23 are discharged evenly over the entire upper region of the interior of the dust cup 16. This permits effective killing of airborne germs captured inside the dust cup 16 over the entire region thereof.

Figure 7:
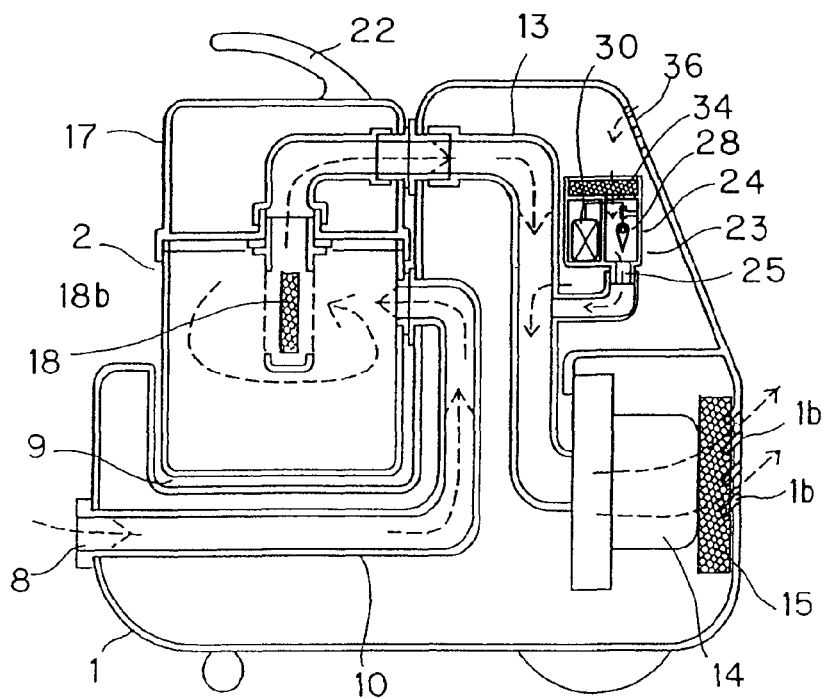
FIG. 7 is a side sectional view showing the internal construction of the body of the electric vacuum cleaner of a third embodiment of the invention.

A third embodiment of the invention will be described below with reference to the drawings. FIG. 7 is a diagram showing the third embodiment of the invention. In this embodiment, an ion generator 23 is disposed along the second suction air passage 13. Specifically, the body casing 24 of the ion generator 23 is disposed along the second suction air passage 13. The ion outflow port 25 formed in the bottom face of the body casing 24 communicates with the second suction air passage 13, and outside air is taken in through air intake holes 36 formed in an upper part of the side wall of the body 1.

In this construction, when the control panel 4 is so operated as to start operation, the electric blower 14 and the ion generating circuit 30 are energized, so that the electric blower 14 starts to be driven to suck air in through the nozzle unit 6 and the ion generating circuit 30 starts to operate to apply a high voltage to the needle-shaped electrode 31.

As a result, first, as the electric blower 14 is driven, the air, containing dust, sucked in through the nozzle unit 6 is introduced, through the hose socket 8, into the body 1. As air is sucked in this way, inside the body 1, as shown in FIG. 7, the air sucked into the first suction air passage 10 is sucked through the inflow pipe 20 into the dust cup 16 while swirling around.

Thus, the stream of air swirls around inside the dust cup 16, with the result that, by the action of centrifugal force, the dust contained in the stream of air is separated from the air and is collected inside the dust cup 16. The air having dust removed therefrom and thus purified is sucked through the filter 18b into the exhaust cylinder 18, is then passed through the exhaust pipe 19, outflow pipe 21, and second coupling member 12 into the second suction air passage 13, and is then passed through the electric blower 14 and deodorizing filter 15 so as to be discharged out of the body 1 through the exhaust opening 1b.

On the other hand, the stream of air passing through the second suction air passage 13 produces a negative pressure near the ion outflow port 25, and thus the air in the rear chamber 28 is sucked into the second suction air passage 13. As a result, air is sucked in through the air intake holes 36 from outside, is then passed through the filter 34, and is then, along with the ions generated in the rear chamber 28, passed through the second suction air passage 13 to the electric blower 14.

Thereafter, the air is passed through the deodorizing filter 15 so as to be discharged out of the body 1 through the exhaust opening 1b. Meanwhile, various germs present in the stream of air are killed by the ions generated by the needle-shaped electrode 31, with the result that the air is purified. The present invention is applicable not only to cyclone-type electric vacuum cleaners but also to electric vacuum cleaners of any other types.

A fourth embodiment of the invention will be described below with reference to the drawings. The first to third embodiments described above deal with an ion generator 231 having a needle-shaped electrode. The ion generator 231 is simply for discharging ions from an electrode as a result of application of a voltage thereto, and thus can be constructed in various manners. The fourth to seventh embodiments described below deal with a grid-shaped ion generator 231 that is constructed differently from the ion generator 23 having a needle-shaped electrode as shown in FIG. 3.

Figure 9:
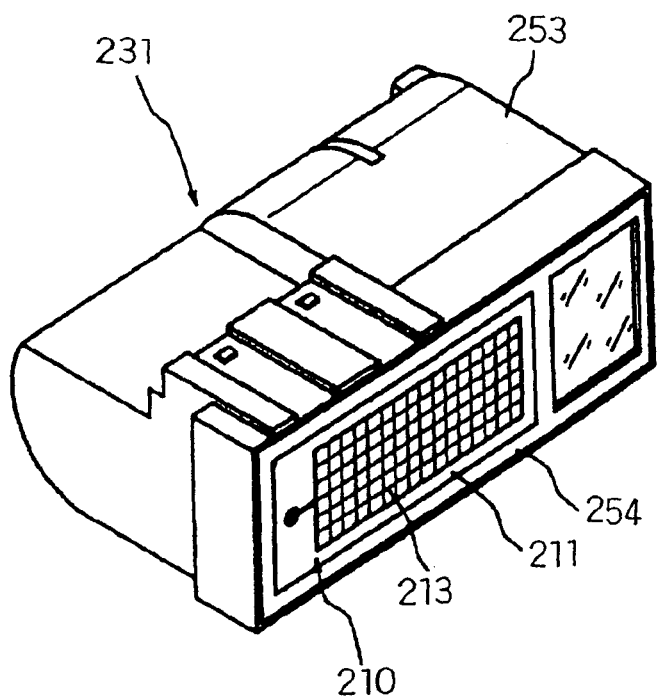
FIG. 9 is an external perspective view of the ion generator used in the electric vacuum cleaner, as seen from the ion generating element side.
Figure 10:
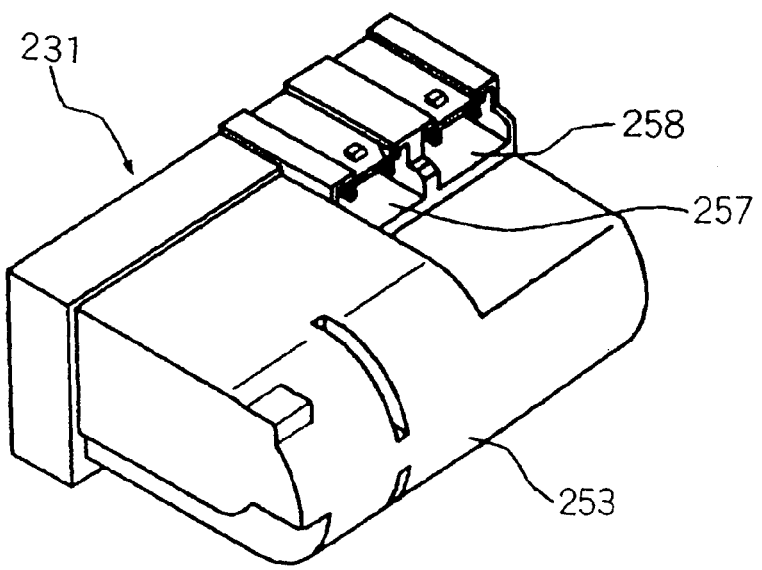
FIG. 10 is an external perspective view of the ion generator, as seen from the side opposite to the ion generating element.
Figure 11:
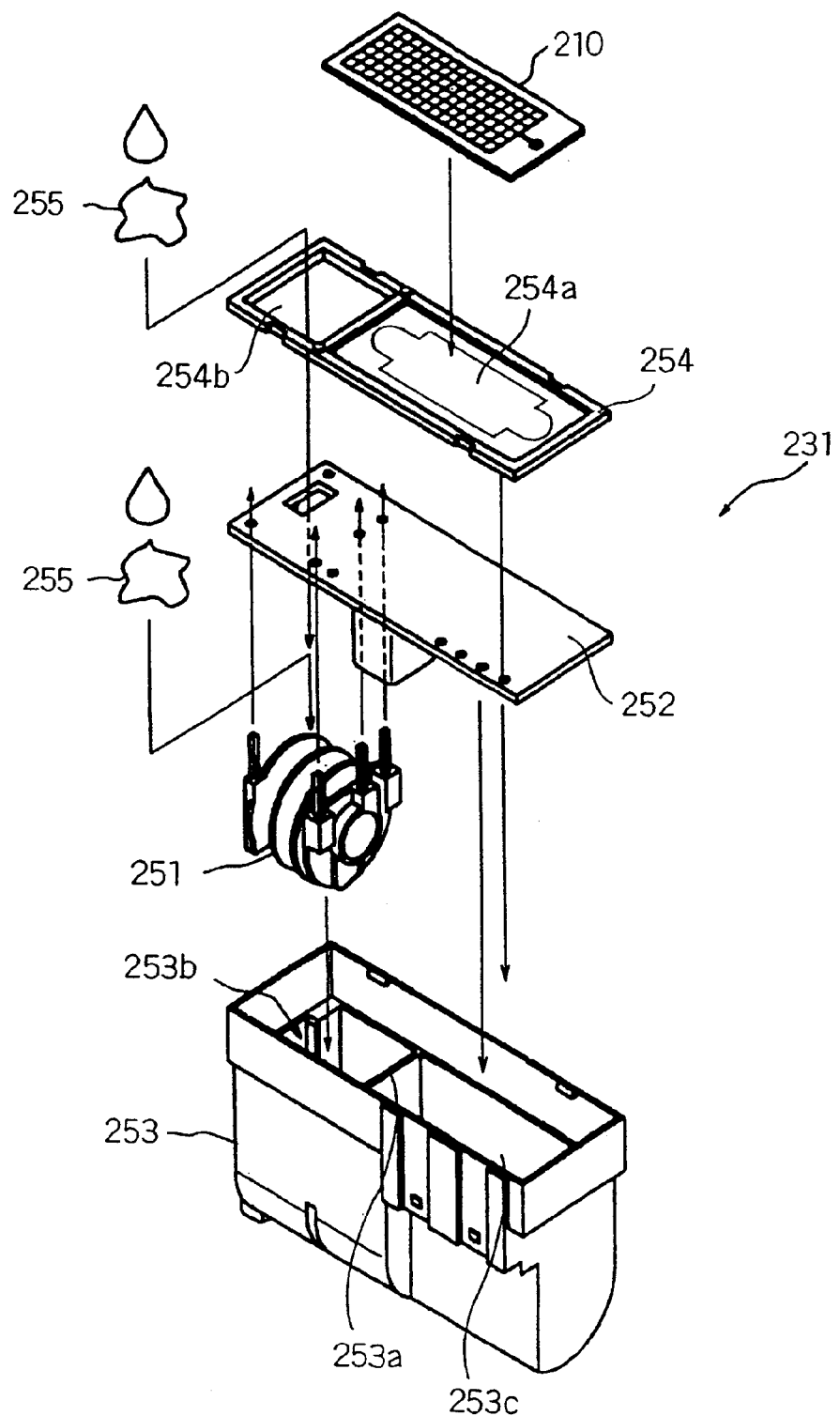
FIG. 11 is an exploded perspective view of the ion generator.
Figure 12A:
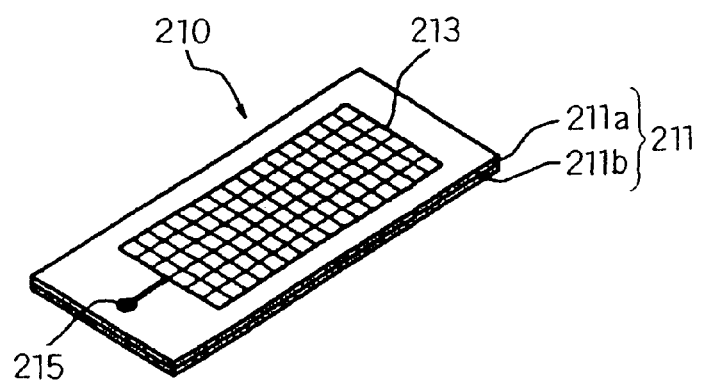
FIG. 12A is an outline perspective view showing the ion generating element of the ion generator.
Figure 12B:
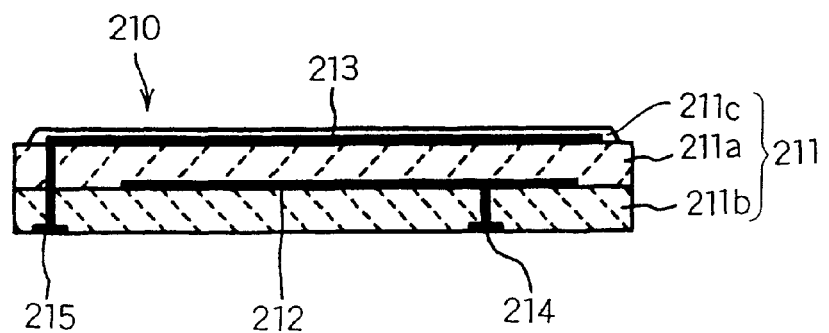
FIG. 12B is a sectional view showing the ion generating element of the ion generator.

First, the construction of the ion generator 231 will be described. FIG. 9 is an external perspective view of the ion generator 231 as seen from the ion generating element 210 side thereof, and FIG. 10 is an external perspective view of the ion generator 231 as seen from the opposite side. FIG. 11 is an exploded perspective view of the ion generator 231, FIG. 12A is an external perspective view of the ion generating element 210, and FIG. 12B is a sectional view of the generating element 210.

The ion generating element 210 includes: a surface electrode 213 laid on the surface of a flat-plate-shaped dielectric 211; a surface electrode contact 215 formed on the surface of the dielectric 211 to permit electric power to be fed to the surface electrode 213; an inner electrode 212 buried inside the dielectric 211 and laid parallel to the surface electrode 213; and an inner electrode contact 214 formed on the surface of the dielectric 211 to permit electric power to be fed to the inner electrode 212. The dielectric 211 is composed of a top plate 211a, a bottom plate 211b, and a surface protection plate 211c.

The ion generator 231, which incorporates the ion generating element 210 structured as described above, is provided with a voltage step-up coil 251, a circuit board 252, a common case 253, and a lid plate 254. The voltage step-up coil 251 has a pair of high-voltage terminals and a pair of input terminals provided on one side of a resin case.

A circuit for generating a waveform for driving the ion generating element 210 is formed on one surface (the lower surface in FIG. 11) of the circuit board 252, and thus on this surface of the circuit board 252 are mounted various circuit components, such as capacitors and semiconductor devices. The circuit board 252 has four connection pins for external connection provided so as to protrude from the one surface.

The common case 253 is box-shaped. The common case 253 has a rectangular opening formed all over one side thereof to permit the circuit board 252 to be inserted therein. On the opposite side thereof, the common case 253 has a bottom part having a semicircular sectional shape. This bottom part is divided into a coil housing 253b and a circuit component housing 253c by a partition wall 253a, which is formed substantially perpendicularly to the length direction and has a predetermined height.

All around the inside of the common case 253, at the same height as the upper edge of the partition wall 253a, a support frame for supporting the circuit board 252 is formed so as to protrude inward. At the rim of the open side of the common case 253, at two separate places on each of the opposite longer sides, depressions are formed with which the lid plate 254 engages.

The lid plate 254 is a flat plate formed of a resin material. In one side of the lid plate 254 along its length, a rectangular depression is formed that corresponds to the ion generating element 210. In this depression is formed a hole 254a, which has an elliptic window hole and a resistive element cavity integrally formed to penetrate the lid plate 254 in positions corresponding to the surface electrode contact 214 and the inner electrode contact 215 of the ion generating element 210.

When the ion generating element 210 is fitted into the aforementioned depression of the lid plate 254 structured as described above, the lid plate 254 integrally holds the ion generating element 210.

To build the ion generator 231, the voltage step-up coil 251, circuit board 252, common case 253, and the lid plate 254 having the ion generating element 210 secured thereto, of which each is structured as described above, are assembled together in the following manner.

First, the voltage step-up coil 251 is inserted, with the aforementioned high-voltage, ground, and input terminals protruding upward, into the coil housing 253b formed in the bottom part of the common case 253. Then, the coil housing 253b is filled with a filling material 255 under a vacuum in such a manner as to prevent entry of bubbles. Thus, a molding for insulation is formed.

Thereafter, after the filling material 255 is dried and cured, the circuit board 252 is inserted into the common case 253 through its top opening. The insertion here is performed in the following manner. First, the component-mounted side of the circuit board 252 is kept down, and the connection holes for connection to the voltage step-up coil 251 are positioned right above the voltage step-up coil 251 secured in the coil housing 253b. Then, the circuit board 252 is inserted until the bottom surface thereof strikes the partition wall 253c and the support frame. After the insertion, the aforementioned high-voltage, ground, and input terminals are, at their one end, welded to their respective positions on the top surface of the circuit board 252. As a result of this welding, the circuit board 252 is supported from below by the support frame and the top edge of the partition wall 253a, and is fixed in position, with the high-voltage, ground, and input terminals serving as the support legs of the circuit board 252, by the voltage step-up coil 251, which in turn is fixed in position by the filling material 255.

After the circuit board 252 is fitted in this way, the lid plate 254, with the ion generating element 210 held therein as described above, is fitted. Here, the fitting is performed in the following manner. The hole 254a formed in one side of the lid plate 254 along its length is positioned right above the window hole formed in the circuit board 252 previously fixed in the common case 253, and then, while the surface of the lid plate 254 on which the ion generating element 210 is held is kept up, the lid plate 254 is fitted into the top opening of the common case 253. Here, the engagement claws formed on opposite edges of the lid plate 254 deform and then retrieve their original shapes to thereby engage with the corresponding depressions formed at the rim of the opening of the common case 253. Thus, the lid plate 254 is fitted at an appropriate distance from the top surface of the circuit board 252 in such a way as to close the opening of the common case 253.

After the fitting, the filling material 255 is introduced through a window hole 254b formed in the lid plate 254 so that the filling material 255 fills the space between the lid plate 254 and the circuit board 252. In this way, the space between the circuit board 252 and the ion generating element 210 is filled with a molding for insulation. When the filling material 255 is dried and cured, the assembly of the ion generator 231 is complete.

The purpose of using a grid-shaped electrode as the surface electrode 213 as shown in FIGS. 12A and 12B is to maximize the quantities of ions generated when a drive voltage is applied thereto. On the other hand, the inner electrode 212 is formed as a strip-shaped electrode of which the center coincides with the center of the surface electrode 213 and which is smaller than the surface electrode 213 in both length and width. This shape also contributes to maximizing the quantities of ions generated.

For example, a top plate 211a and a bottom plate 211b, each about 0.45 mm thick, are laid together to form a dielectric 211 measuring about 15 mm×37 mm×0.9 mm. On the surface of this dielectric 211, conductors, each 0.25 mm wide, are arranged vertically and horizontally with a pitch of 0.8 mm to form a grid-shaped surface electrode 213 measuring about 10.4 mm×28 mm. Moreover, between the top plate 211a and the bottom plate 211b, a sheet-shaped inner electrode 212 measuring about 6 mm×24 mm is formed. When, as a drive voltage, a high-voltage current having a voltage of about 4.6 kV (peak) and a frequency of 22 kHz was applied between those electrodes, it was confirmed that the plasma discharge that occurred between the electrodes 212 and 213 generated over 200,000 ions/cc of positive ions and over 200,000 ions/cc of negative ions at a position 25 cm away from the ion generating element 210. These quantities of ions generated are sufficient for air purification in a typically-sized room in a household.

The quantities of ions generated by the ion generator 231 can be increased by making the ion generating element 210 larger, or by making the drive voltage higher. However, when the drive voltage is increased, the quantity of ozone generated increases accordingly. Thus, it is not preferable to excessively increase the drive voltage, and it is preferable, for example, to intermittently apply the drive voltage so as to reduce the quantity of ozone generated and simultaneously save energy.

In a case where the ion generator 231 constructed as described above is used in one of the electric vacuum cleaners of the embodiments that have already been described and those which will be described later, it is preferable that the ion generator 231 be disposed near the stream of air produced when the electric blower 14 is driven, and that the ion generator 231 be fitted in such a way that the surface thereof on which the ion generating element 210 is fitted faces the stream of air.

In this case, as opposed to in the ion generator 23 shown in FIG. 3, the ion generating element 210 is exposed, and thus can be fitted in a position where it easily faces the stream of air. After the fitting, connection terminals 257 and 258 (see FIG. 10) on the outside of the common case 253 are connected to an unillustrated external power supply and to the control circuit of the electric vacuum cleaner, so that the ion generator 231 generates ions and discharges them in a form mixed with the stream of air produced inside and outside the electric vacuum cleaner.

Here, the positive ions mentioned above are cluster ions each having a plurality of water molecules attached around a hydrogen ion ($H^+$), and are expressed as $H^+(H_2O)_m$ (where m is a natural number). On the other hand, the negative ions are cluster ions each having a plurality of water molecules attached around an oxygen ion ($O_2^-$), and are expressed as $O_2(H_2O)_n$ (where n is a natural number).

After being discharged in a form mixed with the air produced inside and outside the electric vacuum cleaner, those positive and negative ions, as described earlier, flock together around airborne objects (particles, bacteria) present in the air inside the space into which they have been discharged, and chemically react with each other to produce, as an active substance, hydrogen peroxide $H_2O_2$ or hydroxyl radical .OH. Thus, through an oxidation reaction, the ions deactivate airborne particles and kill airborne bacteria. As a result, it is possible to purify the air inside the suction air passage running through the electric vacuum cleaner described below and the air present in the living room where the electric vacuum cleaner is used.

Figure 13:
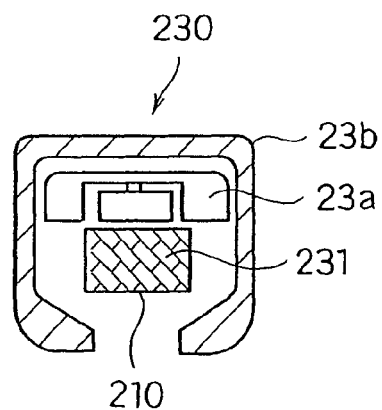
FIG. 13 is an enlarged side sectional view sowing another example of the infernal construction of the ion generator.

As shown in FIG. 13, the ion generator 231 may be provided with an ion discharge fan 23a so that ions are discharged by a stream of air produced as the ion discharge fan 23a rotates. Specifically, the ion generator 231 and the ion discharge fan 23a may be housed in a casing 23b and then, along with an ion generating circuit and a power supplying means, built into an ion generator 230, which is then fitted to an electric vacuum cleaner.

This makes it easy to additionally incorporate an ozone-separating or -absorbing function into the casing 23b, and thus makes its manufacture easy. As a power supplying means, it is possible to use dry cells, rechargeable cells, or the like. This makes it possible to generate and discharge ions independently.

In this way, incorporating the ion discharge fan 23a for discharging ions makes it possible to supply ions irrespective of whether the electric blower 14 is being driven or not. Thus, with the electric vacuum cleaner placed in a place where air needs to be purified, the ion generator 231 and the ion discharge fan 23a can be driven to purify the air in that space. Moreover, by disposing the ion generator 231 and the ion discharge fan 23a in the suction air passage by way of which dust is sucked in through the nozzle unit 6 and air is discharged out of the body 1, it is possible to supply ions more effectively.

Figure 8:
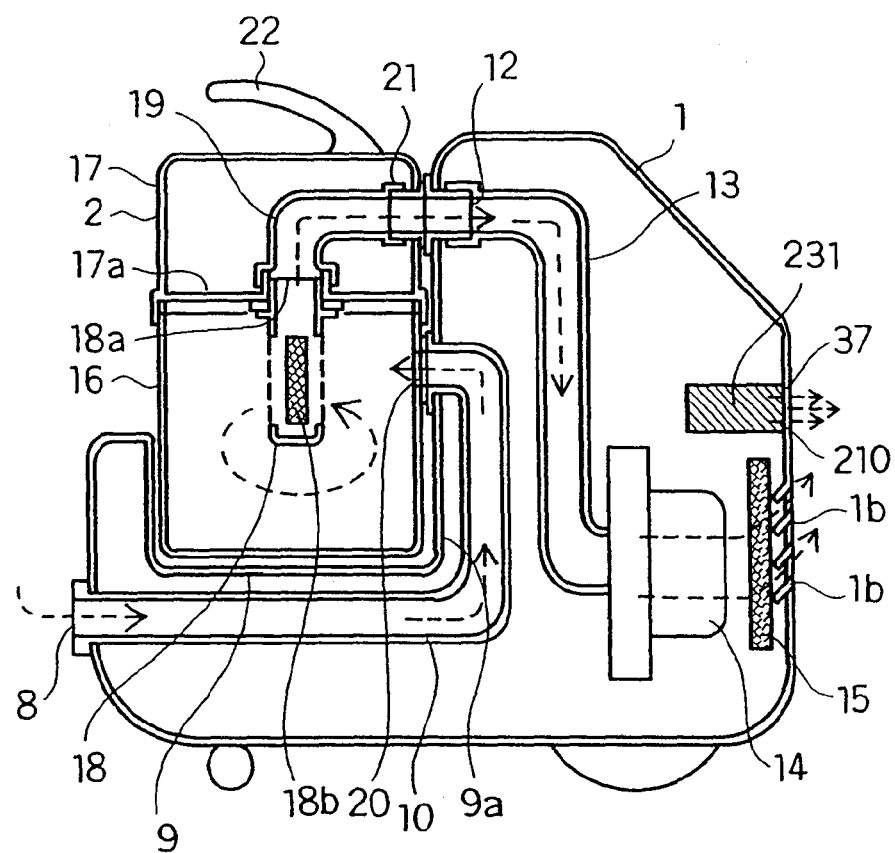
FIG. 8 is a side sectional view showing the internal construction of the body of the electric vacuum cleaner of a fourth embodiment of the invention.

FIG. 8 is a diagram showing a fourth embodiment of the invention. In this embodiment, the ion generator 231 is disposed on the inside of the rear wall of the body 1 so that ions are discharged into the air that is discharged through the exhaust opening 1b, and are thus discharged into the room by that stream of air. Specifically, near the exhaust opening 1b (for example, closely above the exhaust opening 1b), an ion discharge port 37 is formed to penetrate the rear wall of the body 1, and the ion generator 231 is disposed in close contact with the ion discharge port 37.

In this construction, when the control panel 4 (see FIG. 1) is so operated as to start operation, the electric blower 14 and the ion generating circuit (not illustrated) are energized, so that the electric blower 14 starts to be driven to suck air in through the nozzle unit 6 (see FIG. 1) and the ion generating circuit (not illustrated) starts to operate to apply a high voltage to the electrode of the ion generator.

First, as the electric blower 14 is driven, the air, containing dust, sucked in through the nozzle unit 6 is introduced, through the hose socket 8, into the body 1. As air is sucked in this way, inside the body 1, as shown in FIG. 8, the air sucked into the first suction air passage 10 is sucked, through the inflow pipe 20, into the dust cup 16 of the dust collector 2 while swirling around.

Thus, the stream of air swirls around inside the dust cup 16, with the result that, by the action of centrifugal force, the dust contained in the stream of air is separated from the air and is collected inside the dust cup 16. The air having dust removed therefrom and thus purified is sucked through the filter 18b into the exhaust cylinder 18, is then passed through the exhaust pipe 19, outflow pipe 21, and second coupling member 12 into the second suction air passage 13, and is then passed through the electric blower 14 and deodorizing filter 15 so as to be discharged out of the body 1 through the exhaust opening 1b.

The positive and negative ions generated by the ion generator 231 are discharged out of the body 1 through the ion discharge port 37 so as to be mixed with the air near the exhaust opening 1b. As a result, ions are carried by the stream of air discharged through the exhaust opening 1b so as to reach all corners of the room, achieving air purification inside the stream of air and inside the room.

Figure 14:
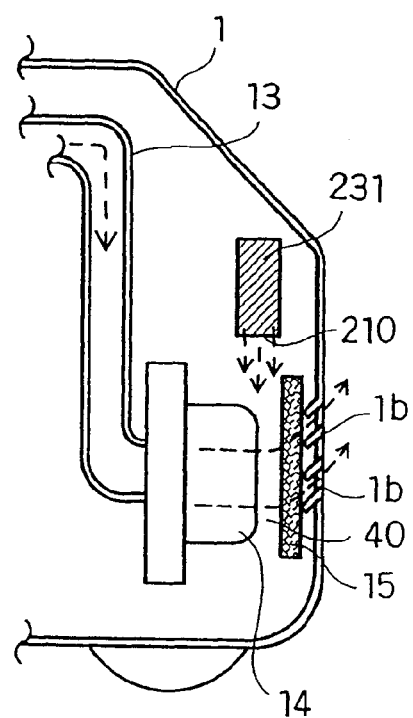
FIG. 14 is a side sectional view around the exhaust opening, showing the internal construction of the body of another embodiment of the electric vacuum cleaner.

As shown in FIG. 14, the electric blower 14 and the deodorizing filter 15 may be disposed at a distance from each other so as to leave a space 40 between the discharge side of the electric blower 14 and the deodorizing filter 15 of the body 1, with the ion generator 231 disposed to point toward the space 40. This permits ions to reach the deodorizing filter 15, and thus makes it possible to kill bacteria settled on the deodorizing filter 15.

Figure 15:
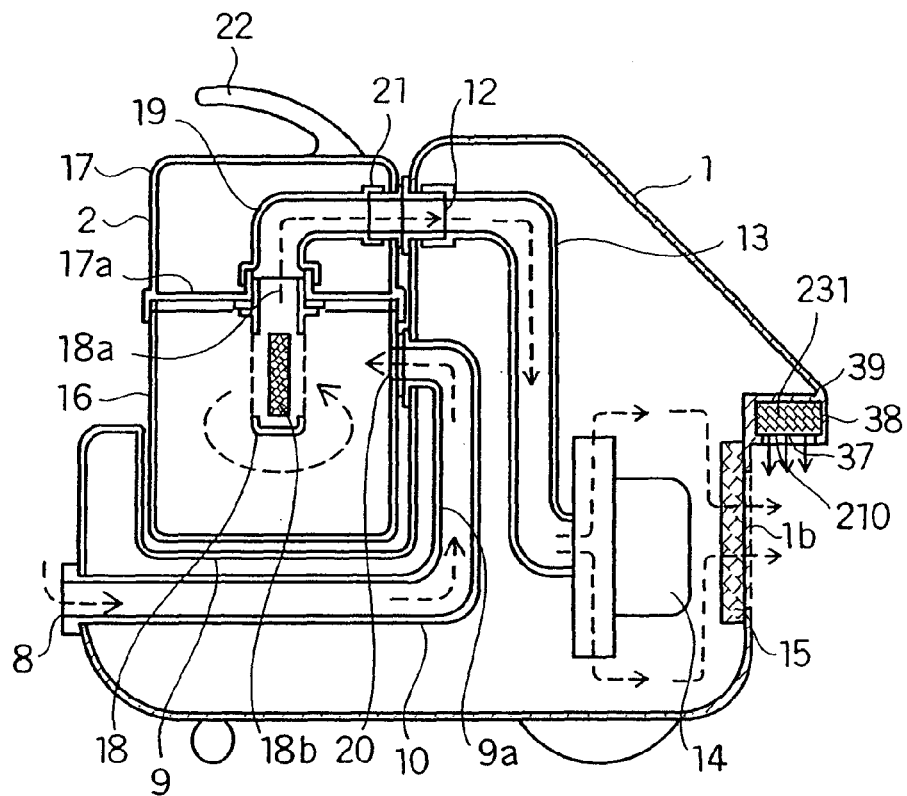
FIG. 15 is a side sectional view showing the internal construction of the body of the electric vacuum cleaner of a fifth embodiment of the invention.

A fifth embodiment of the invention will be described below with reference to the drawings. FIG. 15 is a diagram showing the fifth embodiment of the invention. In this embodiment, the ion generator 231 is disposed on the outside of the rear wall of the body 1, and ions are generated toward the stream of air discharged through the exhaust opening 1b so that ions are discharged into the room by that stream of air.

Specifically, in a rear part of the body 1, a projecting part 39 is formed so as to overhang the exhaust opening 1b, and, below this projecting part 39, an ion generation chamber 38 is formed. The ion generator 231 is deposed inside this ion generation chamber 38. The ion generation chamber 38 is located closely above the exhaust opening 1b, and has an ion discharge port 37 located near the exhaust opening 1b.

In this construction, when the control panel 4 (see FIG. 1) is so operated as to start operation, the electric blower 14 and the ion generating circuit (not illustrated) are energized, so that the electric blower 14 starts to be driven to suck air in through the nozzle unit 6 (see FIG. 1) and the ion generating circuit (not illustrated) starts to operate to apply a high voltage to the electrode of the ion generator.

As a result, first, as the electric blower 14 is driven, the air, containing dust, sucked in through the nozzle unit 6 is introduced, through the hose socket 8, into the body 1. As air is sucked in this way, inside the body 1, as indicated by broken-line arrows in FIG. 15, the air sucked into the first suction air passage 10 is sucked, through the inflow pipe 20, into the dust cup 16 of the dust collector 2 while swirling around. Thus, the stream of air swirls around inside the dust cup 16, with the result that, by the action of centrifugal force, the dust contained in the stream of air is separated from the air and is collected inside the dust cup 16. The air having dust removed therefrom and thus purified is sucked through the filter 18b into the exhaust cylinder 18, is then passed through the exhaust pipe 19, outflow pipe 21, and second coupling member 12 into the second suction air passage 13, and is then passed through the electric blower 14 and deodorizing filter 15 so as to be discharged out of the body 1 through the exhaust opening 1b.

The ions generated by the ion generator 231 are discharged out of the ion generation chamber 38 through the ion discharge port 37 so as to be mixed with the air near the exhaust opening 1b. As a result, ions are carried by the stream of air discharged through the exhaust opening 1b so as to reach all corners of the room, achieving air purification inside the stream of air and inside the room.

Figure 16:
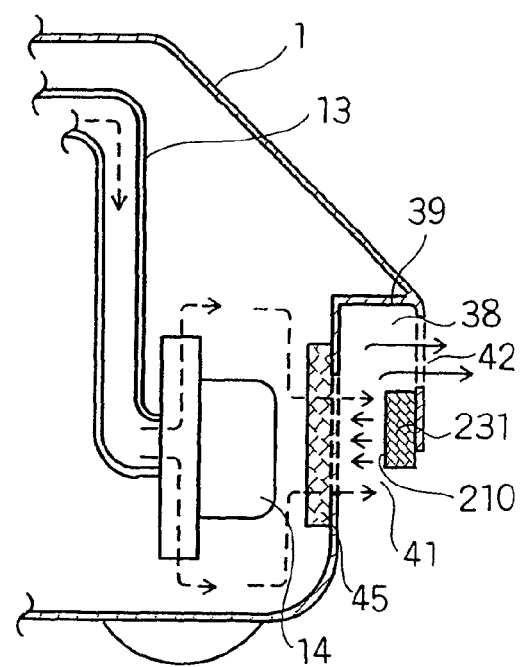
FIG. 16 is a side sectional view around the exhaust opening, showing the internal construction of the body of another embodiment of the electric vacuum cleaner.

As shown in FIG. 16, the ion generation chamber 38 may be so disposed as to discharge ions toward the exhaust opening 1b, with the bottom face of the ion generation chamber 38 made open to form an exhaust opening 41, with the ion generator 231 disposed on the inside of the rear wall thereof, and with an exhaust opening 42 formed near the ion generator 231. This permits ions to be discharged toward the air discharged through the exhaust opening 1b of the body 1, and thus makes it possible to purify the discharged air in a centralized manner so that ions are distributed to all corners of the room through the exhaust openings 41 and 42 by a stream of clean air.

Figure 17:
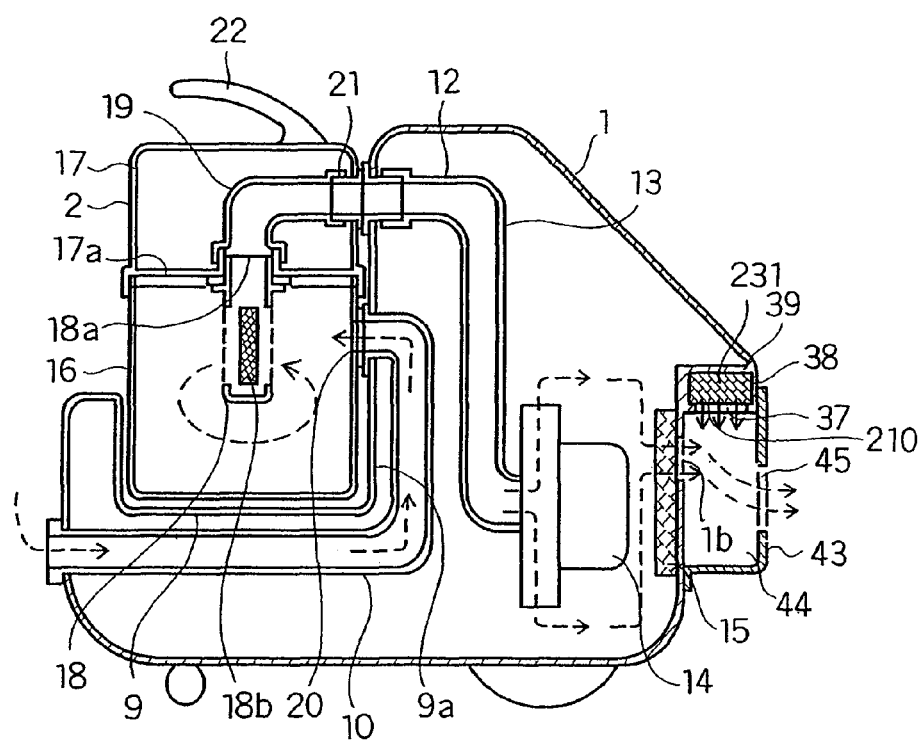
FIG. 17 is a side sectional view showing the internal construction of the body of the electric vacuum cleaner of a sixth embodiment of the invention.

A sixth embodiment of the invention will be described below. FIG. 17 is a diagram showing the sixth embodiment of the invention. In this embodiment, ions are mixed with the air that is discharged through the exhaust opening 1b so as to be discharged into the room by that stream of air. Specifically, the exhaust opening 1b is fitted with a cover 43 so as to form a separate mixing chamber 44 below an ion generation chamber 38 provided in a rear part of the body 1, and an exhaust opening 45 is formed in the rear wall of this cover 43. The ion generation chamber 38 is located closely above the exhaust opening 1b, and has an ion discharge port 37 facing the interior of the mixing chamber 44.

In this construction, when the control panel 4 (see FIG. 1) is so operated as to start operation, the electric blower 14 and the ion generating circuit (not illustrated) are energized, so that the electric blower 14 starts to be driven to suck air in through the nozzle unit 6 (see FIG. 1) and the ion generating circuit (not illustrated) starts to operate to apply a high voltage to the electrode of the ion generator 231. As a result, first, as the electric blower 14 is driven, the air, containing dust, sucked in through the nozzle unit 6 is introduced, through the hose socket 8, into the body 1. As air is sucked in this way, inside the body 1, as shown in FIG. 17, the air sucked into the first suction air passage 10 is sucked, through the inflow pipe 20, into the dust cup 16 of the dust collector 2 while swirling around.

Thus, the stream of air swirls around inside the dust cup 16, with the result that, by the action of centrifugal force, the dust contained in the stream of air is separated from the air and is collected inside the dust cup 16. The air having dust removed therefrom and thus purified is sucked through the filter 18b into the exhaust cylinder 18, is then passed through the exhaust pipe 19, outflow pipe 21, and second coupling member 12 into the second suction air passage 13, and is then passed through the electric blower 14 and deodorizing filter 15 so as to be discharged through the exhaust opening 1b into the mixing chamber 44. The air remains in the mixing chamber 44 for a while, and is then discharged through the exhaust opening 45 into the room.

The ions generated by the ion generator 231 are drawn into the mixing chamber 44 by the stream of air passing therethrough so as to be mixed with the air inside the mixing chamber 44. As a result, inside the mixing chamber 44, the ions are mixed evenly with the air discharged through the exhaust opening 1b. This makes it possible to purify the discharged air in a centralized manner so that ions are distributed to all corners of the room through the exhaust opening 45 by a stream of clean air.

Figure 18:
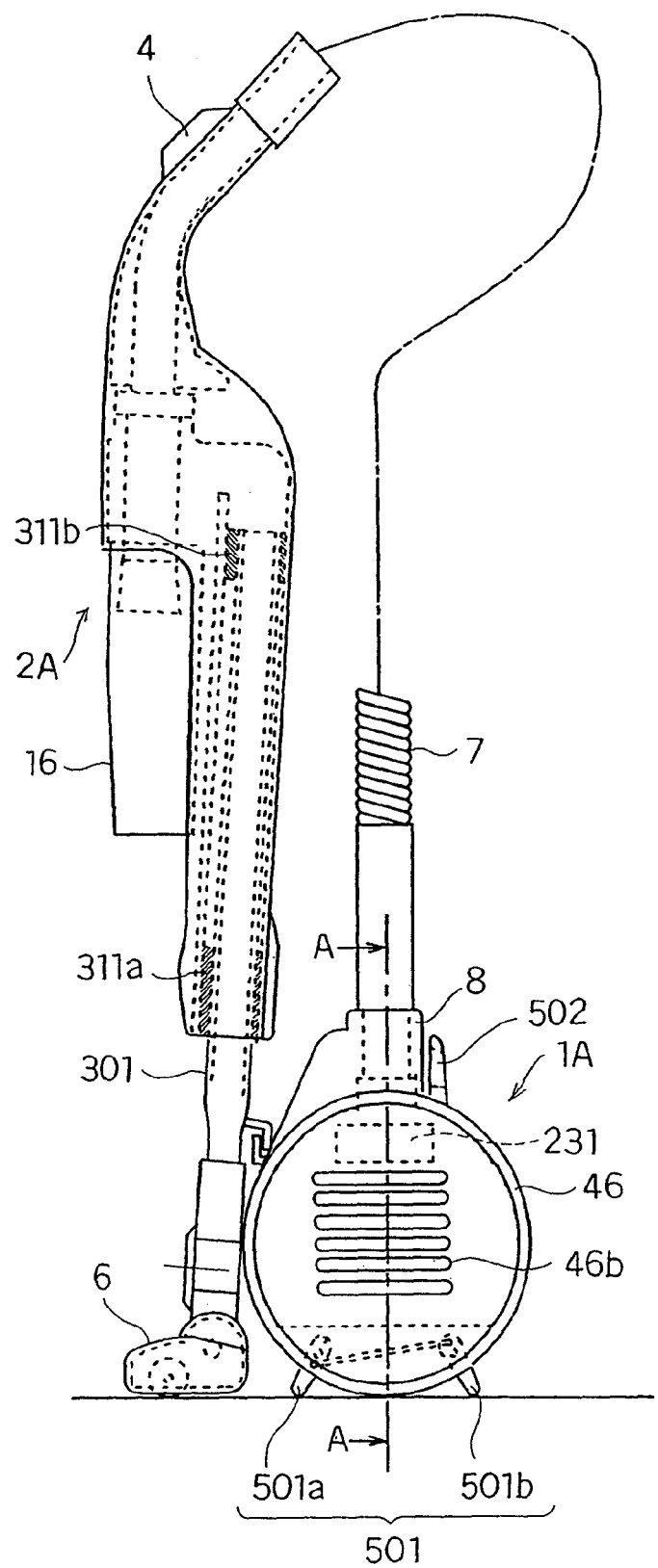
FIG. 18 is a vertical sectional view showing the internal construction of the body, in its rear part, of the electric vacuum cleaner of a sixth embodiment of the invention.
Figure 19:
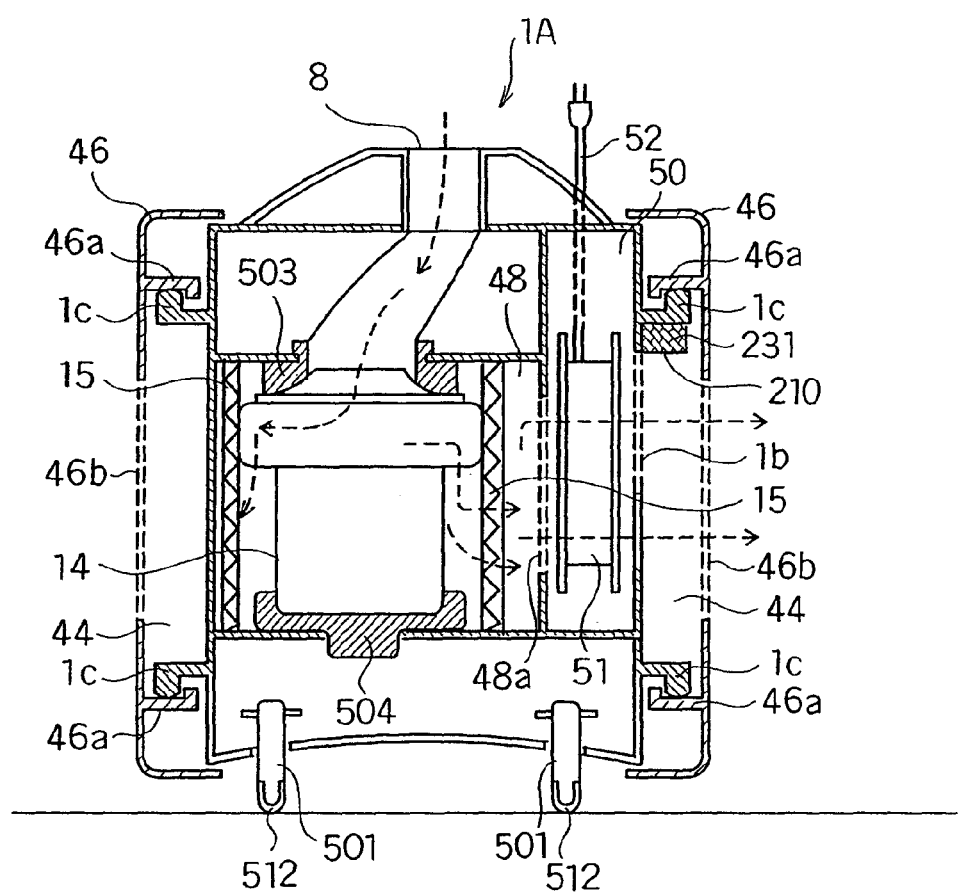
FIG. 19 is a sectional view taken along line A-A shown in FIG. 18.

FIG. 18 is an external view of the electric vacuum cleaner of a seventh embodiment of the invention, showing its state during storage. FIG. 19 is a sectional view of the body shown in FIG. 18, taken along line A-A. The body 1A of the electric vacuum cleaner of this embodiment incorporates an electric blower 14, is provided with casters 46 on both sides, has a mixing chamber 44 formed by the casters 46, and incorporates an ion generator 231. The body 1A is freely movable in all directions. Moreover, a dust collector 2A is disposed between the body 1A and a nozzle unit 6. To the nozzle unit 6 is connected a suction pipe 301, which is sealed with seals 311a and 311b and is slidably provided relative to the dust collector 2A.

Figure 21:
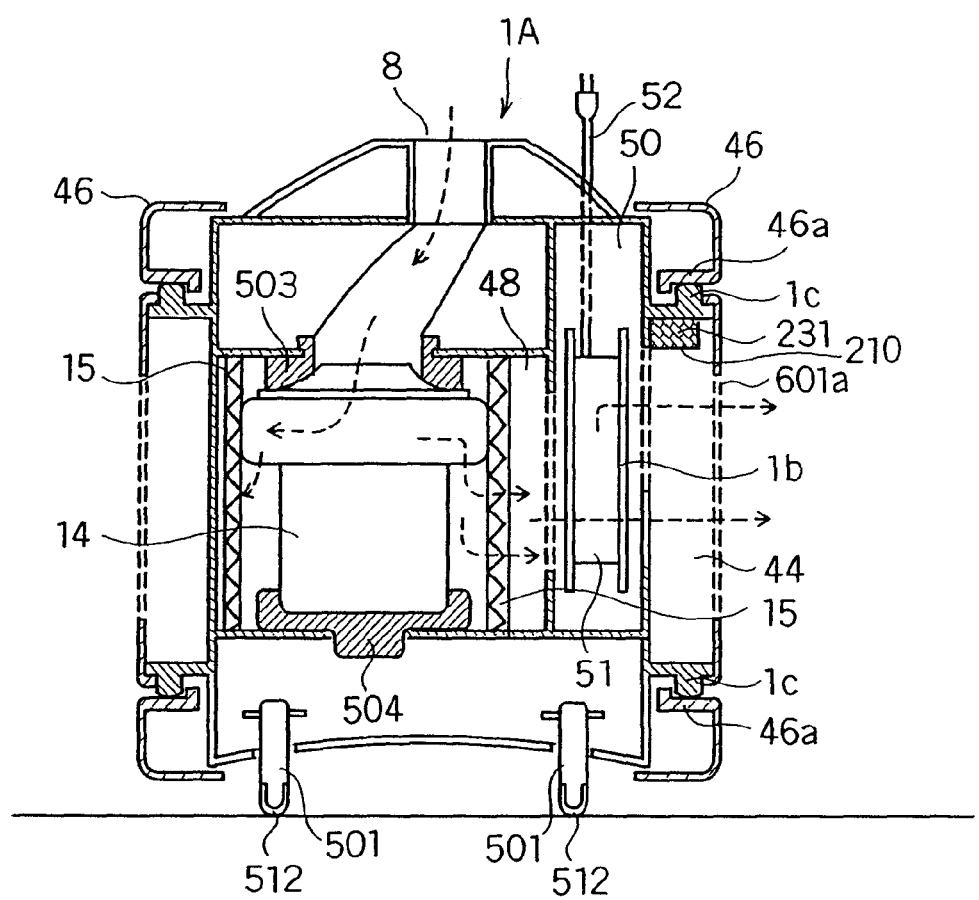
FIG. 21 is a sectional view taken along line A-A shown in FIG. 18, showing another example of the electric vacuum cleaner.

Alternatively, as shown in FIG. 21, the casters 46 may be provided only around the periphery, with caster covers 601 provided inside them so as to form an ion mixing chamber 44. This permits the ion generator 231 to be maintained easily with only the covers 601 removed.

The stream of air sucked in through the nozzle unit 6 is passed through a hose socket 8, the electric blower 14, a filter 15, and a cord reel 51 so as to be discharged through a ventilation openings 46b formed in the casters 46. The filter 15 is so arranged as to enclose the electric blower 14. This helps reduce the noise produced by the electric blower 14, and makes it possible to adopt a filter with a large area, contributing to good ventilation efficiency.

Thus, it is possible to arrange a HEPA filter with extra fine ventilation pores such as to catch dust as small as 1 μm or less. The outer circumference of the filter 15 may be covered with a soundproof material such as urethane to achieve securer soundproofing. The electric blower 14 is held on the body 1A by way of damping members 503 and 504 formed of rubber or the like.

During storage, the electric vacuum cleaner is leaned on stands 501. As shown in FIG. 18, the stands 501 are provided in pairs; specifically, for each of the casters 46, two stands 501a and 501b are provided on either side of its rolling direction so as to be rotatable about rotation shafts 511a and 511b, respectively. Moreover, the stands 501a and 501b are coupled together by couplers 505 (see FIGS. 20A and 20B), and are loaded by springs 506 with a force that tends to cause them to pop outside the casters. The body 1A of this type is freely movable in all directions, and is therefore, during storage, prevented from rolling by the stands 501.

Figure 20A:
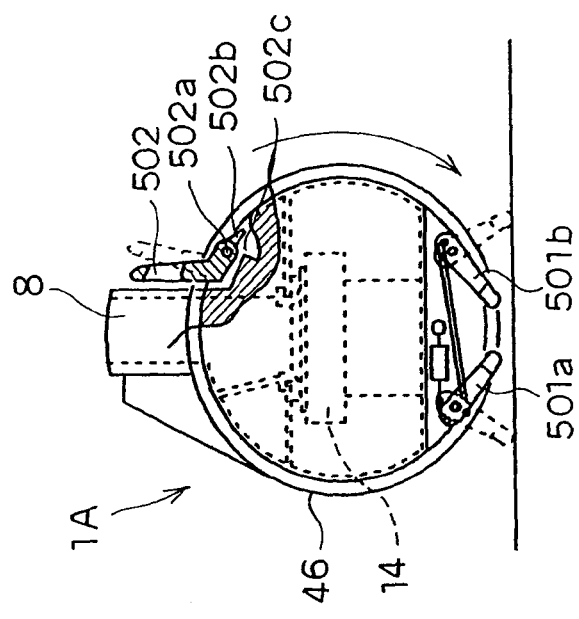
FIG. 20A is a side view showing the posture of the body of the electric vacuum cleaner during cleaning operation.

FIG. 20A is a side view of the body 1A, showing its posture during cleaning operation. In this state, the stands 501 are kept away from the floor to permit the casters 46 to roll and thereby permit the body 1A to freely move. Thus, the stands 501 do not hamper cleaning. When the body 1A is rotated in the direction indicated by the arrow, the stands 501a make contact with the floor, then rotate about the rotation shafts 511a, and thus retract into the body 1A. As the stands 501a rotate about the rotation shafts 511a, the stands 501b, which are coupled thereto by the rods 506, also rotate about the rotation shafts 511b in their retracting direction.

Figure 20B:
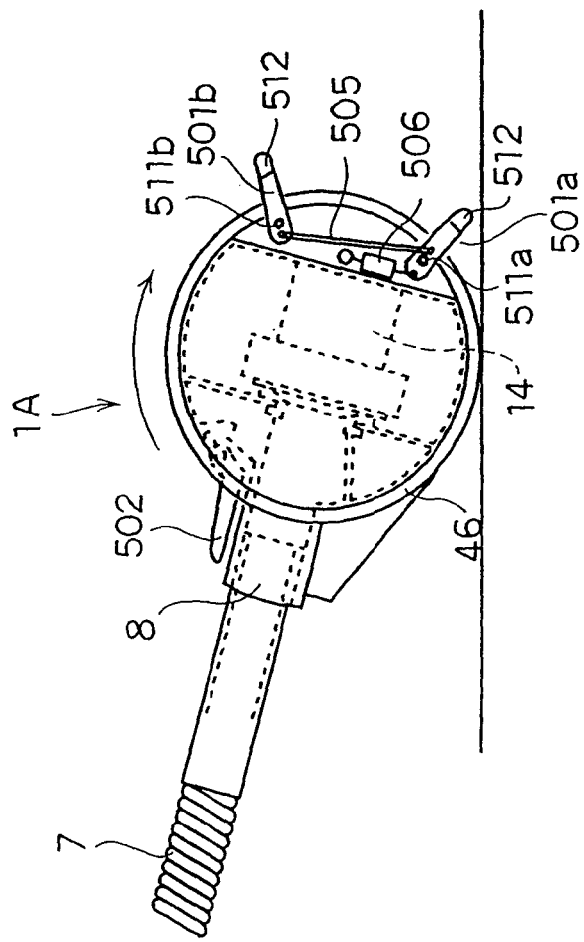
FIG. 20B is a side view showing the posture of the body of the electric vacuum cleaner during storage.

When the body 1A is rotated further, as shown in FIG. 20B, all the stands 501 are retracted. When the stands 501 are located right below, all the stands 501a and 501b are, at their ends, in contact with the floor. Even when the body 1A is rotated further in the direction indicated by the arrow until the stands 501a come off the floor, the stands 501b remain in contact with the floor, and thus none of the stands 501 prop outside the body 1A. This permits smooth rotation of the body 1A. The stands 501 are fitted, at their ends, with damping members 512 formed of a damping material such as rubber or urethane to prevent impact and damage resulting from collision with the floor.

In an upper part of the body 1A, opposite to the stands 501, is provided a handle 502 that permits the electric vacuum cleaner to be carried around. As described above, even in the state shown in FIG. 20B, the stands 501 are in contact with the floor, and therefore, for storage, the body 1A needs to be lifted upward so that the ends of the stands 501 come off the floor to permit the stands 501 to return to their original position under the force exerted by the springs 506. That is, by lifting up the handle 502 to permit the body 1A to come off the floor, it is possible to return the stands 501 to their original position.

Figure 30:
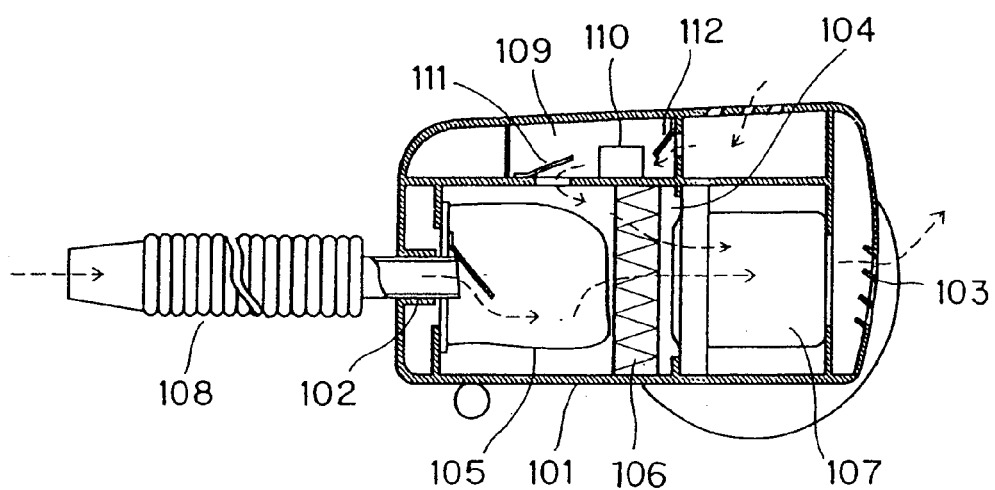
FIG. 30 is an external side sectional view of a conventional electric vacuum cleaner.

The handle 502 is rotatable about a rotation shaft 502a. To return the stands 501 to their original position outside the casters 46 for storage, the handle 502 is rotated to the position indicated by broken lines in FIG. 30B and is then lifted up. A locking means is provide to prevent the handle 502 from rotating beyond a predetermined position.

A projection 502b is formed on the handle 502, and a recess 502c that engages therewith is formed in the body 1A. Thus, when the handle 502 is lifted up, the projection 502b makes contact with the recess 502c so that the handle 502 is held in the position indicated by the broken lines in FIG. 20B. This prevents instability of the body 1A when it is lifted up. Moreover, then, the ends of the stands 501 remain substantially parallel to the floor, permitting secure storage on the floor.

When the handle 502 is let go, it returns, with the help of a spring (not illustrate) or the like, to the position indicated by the solid lines. Here, the electric vacuum cleaner may be so configured as to recognize the storage state to drive the ion generator 231 independently for a predetermined length of time. This permits purification to be performed automatically for a predetermined length of time inside a comparatively airtight space such as the storage space.

Figure 22:
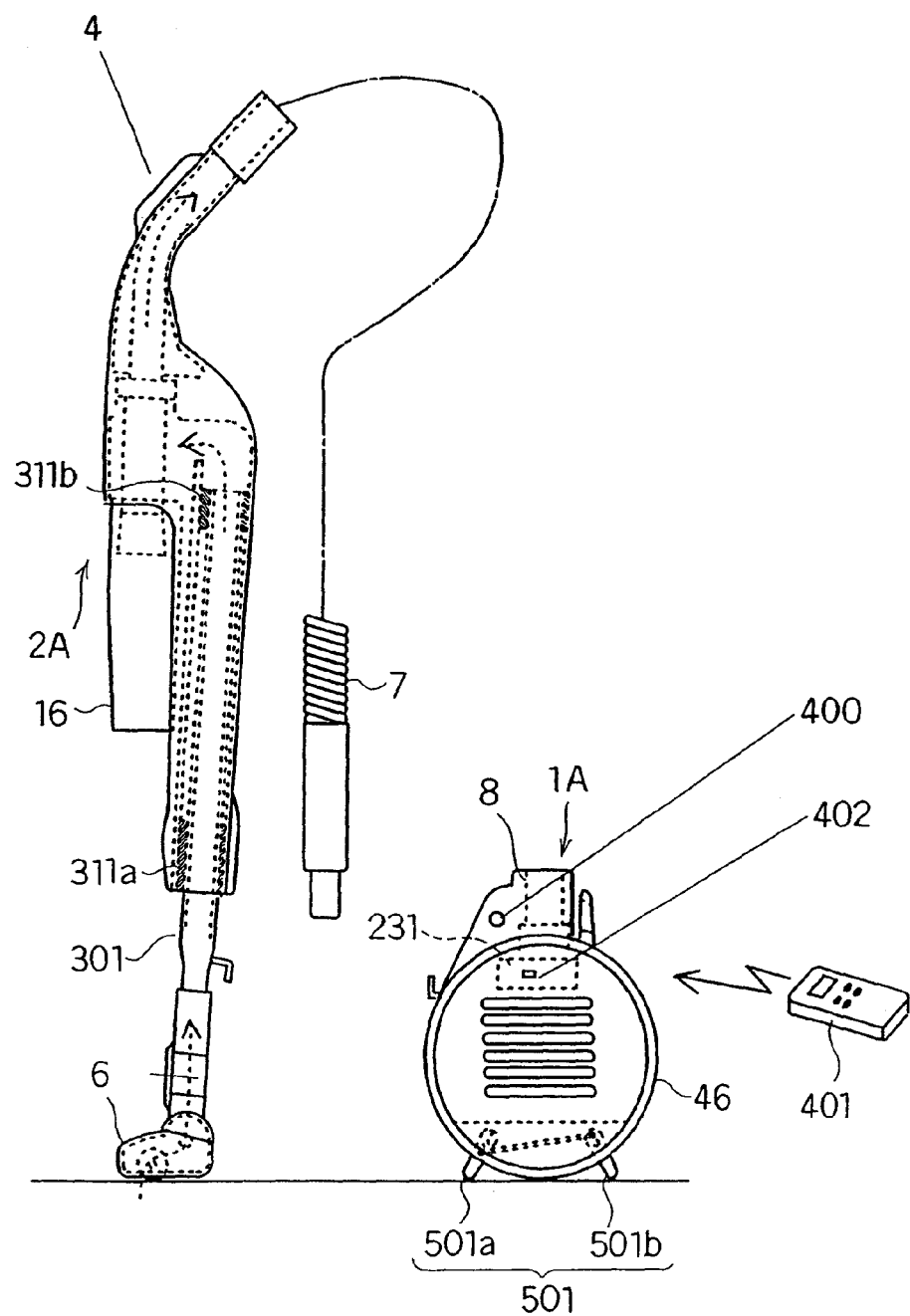
FIG. 22 is a vertical sectional view showing the internal construction of the body, in its rear part, of still another example of the electric vacuum cleaner.

Alternatively, as shown in FIG. 22, the body 1A may be provided with, independently of the control panel 4 for the electric vacuum cleaner, a drive switch 400 for driving the electric blower 14 and the ion generator 231. With this construction, even in a space other than the aforementioned storage space, for example in a closet, the body 1A can be placed with the connection hose 7 removed, and the drive switch can be turned on so that the air inside this space is sucked in and discharged and meanwhile the generated positive and negative ions are discharged into the space in order to achieve purification in the space.

In this case, it is preferable that, after the drive switch 400 is so operated as to turn the power on, the electric blower 14 and the ion generator 231 be driven for a predetermined length of time (for example, 30 minutes). Thus, it is preferable to provide a time control circuit (not illustrated) to permit the setting of the driving time.

The drive switch 400 may be provided directly on the body 1A, or may be provided in the form of a remote control system for remotely controlling the body 1A, with a receiver 402 provided on the body 1A and a transmitter 401 provided as a separate unit. With such a remote control system, even when the body 1A is placed in a narrow space as in a closet, the user can drive the electric blower 14 and the ion generator 231 by operating the remote control unit. This helps further enhance the usability.

Figure 29A:
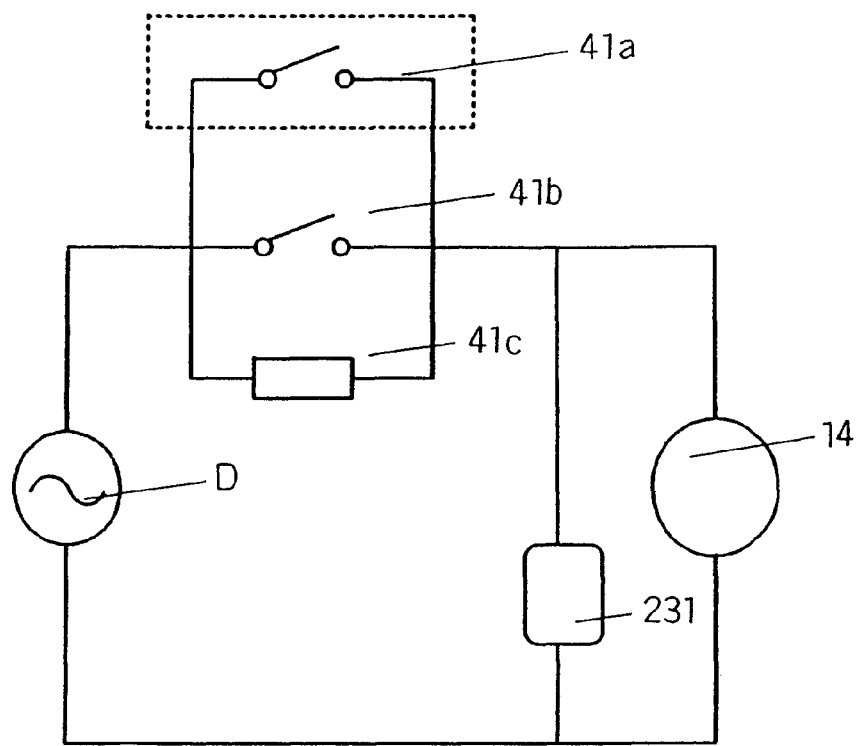
FIG. 29A is a circuit diagram of the control circuit for controlling the electric blower and ion generator in an electric vacuum cleaner according to the invention, showing an example of the control circuit that drives the electric blower and ion generator simultaneously.
Figure 29B:
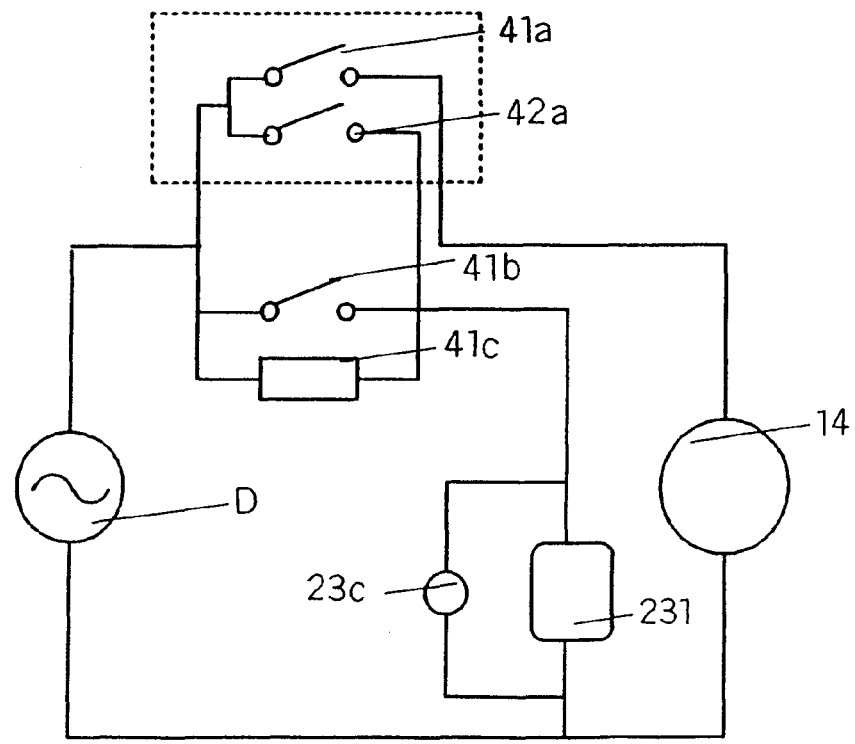
FIG. 29B is a circuit diagram of the control circuit for controlling the electric blower and ion generator in an electric vacuum cleaner according to the invention, showing an example of the control circuit used when the ion generator shown in FIG. 13 is provided in the body.

FIGS. 29A and 29B show examples of the control circuit for controlling the electric blower and the ion generator. FIG. 29A shows an example of the control circuit for simultaneously driving the electric blower 14 and the ion generator 231 housed in the body 1A described above. On the control panel 4 (see FIG. 22) is provided a switch 41a that is connected in series with both the electric blower 14 and the ion generator 231.

Likewise, as the drive switch 400 (see FIG. 22) is provided a switch 41b that is connected in series with both the electric blower 14 and the ion generator 231. Moreover, the remote control system, composed of the transmitter 401 and the receiver 402 (see FIG. 22), includes a switch 41c that is connected in series with both the electric blower 14 and the ion generator 231.

It is preferable that the switches 41a and 41b be so structured that their contact is closed or opened as a turning-on or -off operation is performed on the control panel 4 or the drive switch 400. On the other hand, it is preferable that the switch 42c be built as an electronic circuit switch that is controlled according to a signal fed from the receiver 402 as a turning-on or -off operation is performed on the remote control unit.

Through the operation of the control circuit described above, when the control panel 4, the drive switch 400, or the remote control unit is so operated as to turn the power on, the corresponding switch 41a, 41b, or 41c is closed. As a result, electric power starts to be supplied from a power supply D to the electric blower 14 and the ion generator 231, so that the electric blower 14 and the ion generator 231 start to be driven.

On the other hand, when the control panel 4, the drive switch 400, or the remote control unit is so operated as to turn the power off, the corresponding switch 41a, 41b, or 41c is opened. As a result, electric power stops being supplied from the power supply D to the electric blower 14 and the ion generator 231, so that the electric blower 14 and the ion generator 231 stop being driven.

Thus, for example, in a case where air is purified while the interior of the room is cleaned, or in a case where the air in a space such as a closet is sucked in and discharged so as to be purified, whichever of the switches suits the purpose can be operated to drive the electric blower 14 and the ion generator 231.

FIG. 29B shows an example of the control circuit used when, in place of the ion generator 231, the ion generator 230 shown in FIG. 13 is provided in the body 1A. On the control panel 4 are provided a switch 41a that is connected in series with the electric blower 14 and a switch 42a that is connected in series with the ion generator 231 of the ion generator 230 and with the motor 23c of the ion discharge fan 23a.

As the drive switch 400 is provided a switch 41b that is connected in series with the ion generator 231 of the ion generator 230 and with the motor 23c of the ion discharge fan 23a. Likewise, the remote control system, composed of the transmitter 401 and the receiver 402 (see FIG. 22), includes a switch 41c that is connected in series with the ion generator 231 of the ion generator 230 and with the motor 23c of the ion discharge fan 23a.

It is preferable that the switches 41a and 42a be so structured that their contact is closed or opened as a turning-on or -off operation is performed on the control panel 4. In this case, in response to a turning-on or -off operation performed on the control panel 4, the switches 41a and 42a may be closed or opened simultaneously.

Alternatively, the switches 41a and 42a may be so controlled that, in response to a turning-on operation performed on the control panel 4, the switch 42a is closed first and then the switch 41a is closed and, in response to a turning-off operation performed on the control panel 4, the switch 41a is opened first and then the switch 42a is opened. Alternatively, an unillustrated timer control circuit may be provided that so controls that, when a turning-off operation is performed on the control panel 4, the switch 41a is opened first and then, a predetermined length of time thereafter, the switch 42a is opened.

The control panel 4 may be so configured that the switches 41a and 42a can be operated individually. With the configuration described above, flexible control is possible, for example, by first stopping the driving of the electric blower 14 and then, with a delay, stopping the driving of the ion generator. This makes it possible to further purify the air floating around after being discharged by the electric blower 14.

It is preferable that the switch 41b be so structured that its contact is closed or opened as a turning-on or off operation is performed on the drive switch 400. The switch 41b may be so structured that, when closed, it is opened a predetermined length of time thereafter by an unillustrated time control circuit. It is preferable that the switch 41c be built as an electronic circuit switch that is controlled according to a signal fed from the receiver 402 as a turning-on or -off operation is performed on the remote control unit. The switch 41c may be so structured that, when closed, it is opened a predetermined length of time thereafter by an unillustrated time control circuit.

When the control panel 4 is so operated that the switches 41a and 42a are closed simultaneously, electric power starts to be supplied from the power supply D to the electric blower 14, to the ion generator 231 of the ion generator 230, and to the motor 23c of the ion discharge fan 23a, so that these start to be driven. When the drive switch 400 or the remote control unit is so operated that the corresponding switch 41b or 41c is closed, electric power start to be supplied to the ion generator 231 of the ion generator 230 and to the motor 23c of the ion discharge fan 23a, so that these start to be driven.

Accordingly, for the purpose of cleaning a room and purifying air, the control panel 4 can be operated so that the electric blower and the ion generator 230 are driven simultaneously. On the other hand, since the ion generator 230 is so configured as to be able to discharge ions on its own, for the purpose of discharging ions into a room without cleaning it, the drive switch 400 or the remote control unit can be operated so that the ion generator 230 alone is driven.

In this construction, when the control panel is so operated as to start operation, the electric blower 14 and the ion generating circuit (not illustrated) are energized, so that the electric blower 14 starts to be driven to suck air in through the nozzle unit 6 (see FIG. 1) and the ion generating circuit (not illustrated) starts to operate to apply a high voltage to the electrode of the ion generator 231.

As a result, first, as the electric blower 14 is driven, the air, containing dust, sucked in through the nozzle unit 6 is introduced, through the suction pipe 301, into a dust cup 16 while swirling around. Thus, the stream of air swirls around inside the dust cup 16, with the result that, by the action of centrifugal force, the dust contained in the stream of air is separated from the air and is collected inside the dust cup 16.

The air having dust removed therefrom and thus purified is passed through the hose socket 8 into the body 1A, and is then introduced, through the electric blower 14, deodorizing filter 15, and ventilation opening 48a, into a cord housing 50, where the air cools the cord reel 51. This air is discharged through the exhaust opening 1b into the mixing chamber 44, where the air remains for a while. The air is then discharged out of the body 1 through the exhaust opening 46b. In the cord housing 50 and the mixing chamber 44 may be arranged, other than the cord reel 51, any component, such as a circuit (not illustrated), that generates heat. This permits such a heat-generating component to be cooled with the stream of air.

The ions generated by the ion generator 231 are discharged into the mixing chamber 44 so as to be mixed with the air inside it. As a result, inside the mixing chamber 44, the ions are mixed evenly with the air discharged through the exhaust opening 1b. This makes it possible to purify the discharged air in a centralized manner so that ions are distributed to all corners of the room through the exhaust opening 45 by a stream of clean air.

Furthermore, in this embodiment, the mixing chamber 44 can be formed inside the casters 46 pivoted on the side walls of the body 1. This permits the use of existing components without changing the design of conventional electric vacuum cleaners. This helps keep the product prices low.

Figure 23:
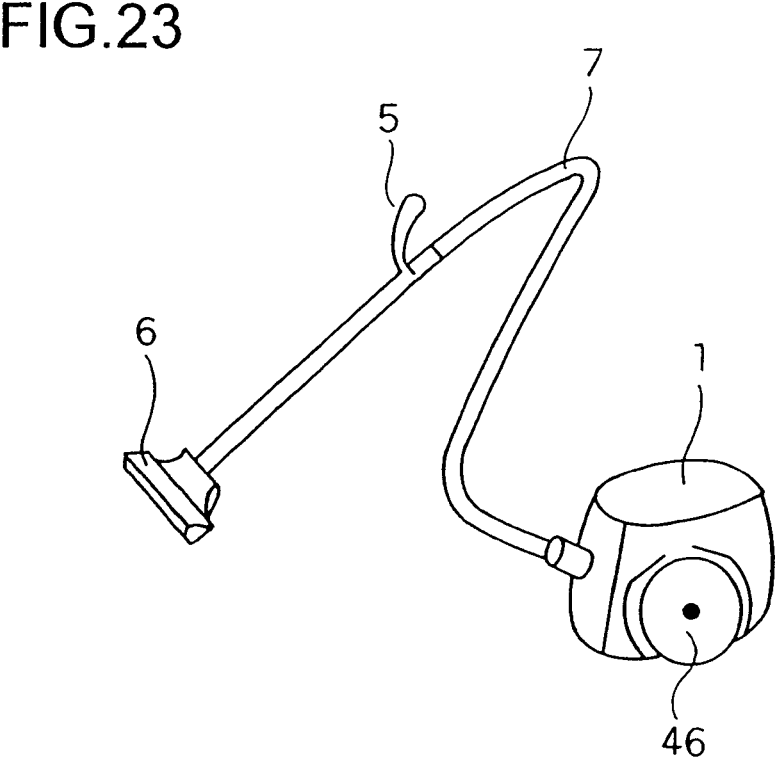
FIG. 23 is an external perspective view showing the electric vacuum cleaner of an eighth embodiment of the invention.

The descriptions given thus far deal only with constructions including a cyclone-type dust collecting device and an ion generator. It is, however, also possible to obtain similar effects, as will be described below, with the type of electric vacuum cleaner that collects dust by passing air through (i.e., by filtering it with) a dust collection bag 2A formed of cloth or paper. An eighth embodiment of the invention will be described below with reference to the drawings. FIG. 23 is an overall perspective view of the electric vacuum cleaner of the eighth embodiment of the invention. As shown in FIG. 23, the electric vacuum cleaner has a body 1, casters 46, a hose 7, a handle 5, and a nozzle unit 6.

Figure 24:
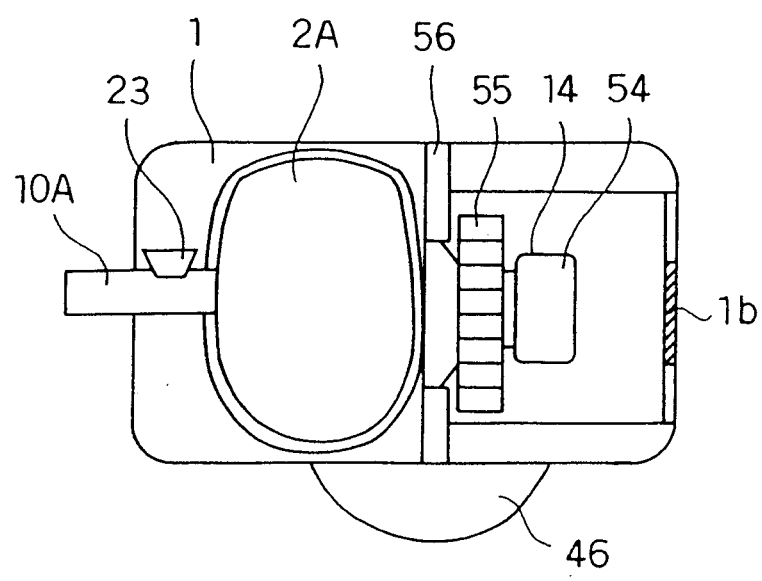
FIG. 24 is a side sectional view showing the internal construction of the body of the electric vacuum cleaner.

FIG. 24 is a sectional view of the body of the electric vacuum cleaner. The body 1 shown in FIG. 24 is provided with a first suction passage 10A, an electric blower 14 that drives a motor 54 to rotate a fan 55 and thereby produces a suction stream of air, and a dust collection bag 2A that collects dust that has been sucked in. The electric blower 14 is fixed inside the body 1 by the use of a support member 56 having a circular opening formed at the center. Moreover, an ion generator 23 (231) that generates ions is disposed in the first suction passage 10A, which runs from a hose socket 8 to the dust collector 2A.

When a carpet or the like is cleaned with the electric vacuum cleaner having its body 1 constructed as described above, dust, such as animal hair, house mites, mold, and pollen, is sucked in and is collected in the dust collection bag 2A. When the air containing such dust passes through the first suction passage 10A, by the action of the positive and negative ions discharged from the ion generator 23, the odor-producing substances and allergenic chemical substances contained in the air are decomposed. As a result, the exhaust air discharged out of the electric vacuum cleaner returns to the room as air that is free from not only dust but also odor-producing substances.

Figure 25:
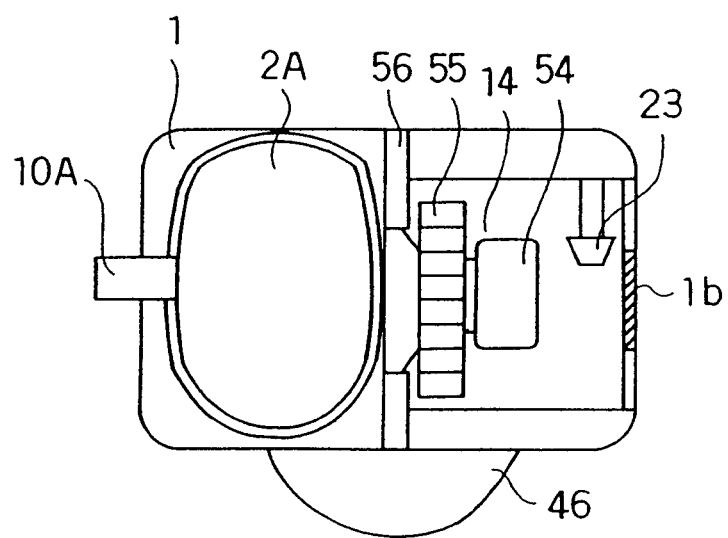
FIG. 25 is a side sectional view showing the internal construction of the body of the electric vacuum cleaner of a ninth embodiment of the invention.

FIG. 25 is a sectional view of the body of the electric vacuum cleaner of a ninth embodiment of the invention. The body shown in FIG. 25 incorporates a first suction passage 10A, an electric blower 14 that drives a motor 54 to rotate a fan 55 and thereby produces a suction stream of air, and a dust collection bag 2A that collects dust that has been sucked in. Moreover, an ion generator 23 is disposed between the dust collection bag 2A and an exhaust opening 1b.

When a carpet or the like is cleaned with the electric vacuum cleaner having its body 1 constructed as described above, dust, such as animal hair, house mites, mold, and pollen, is sucked in and collected in the dust collection bag 2A, and the chemical substances such as odor-producing substances contained in the air having dust removed therefrom are decomposed by the action of the positive and negative ions discharged from the ion generator 23. Furthermore, ions are discharged into the room by the stream of exhausted air so as to eliminate chemical substances remaining in the room.

Figure 26:
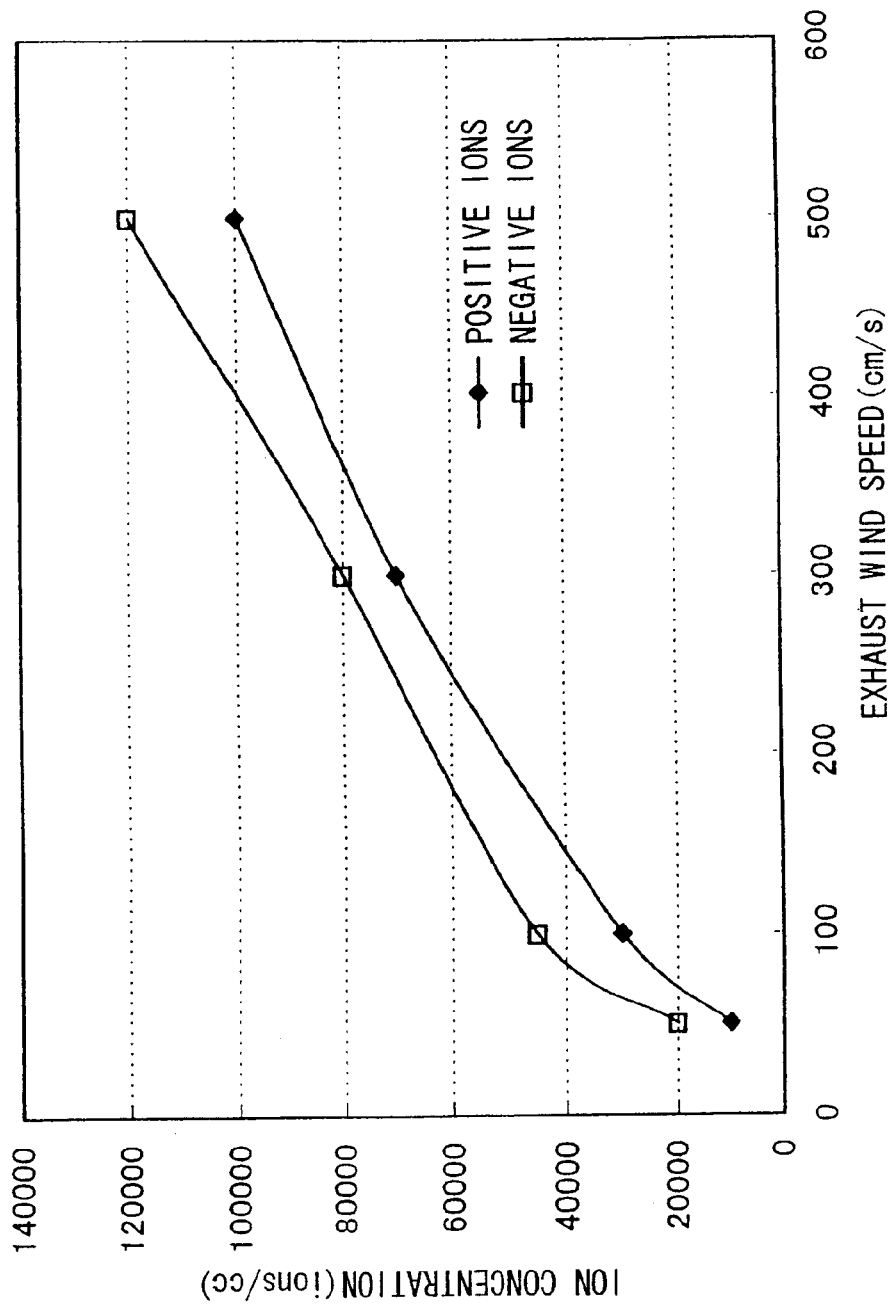
FIG. 26 is a diagram showing the measurements of the concentrations of ions generated by the electric vacuum cleaner.

FIG. 26 shows the result of measurements of the concentrations of ions generated by the electric vacuum cleaner shown in FIG. 25. The concentrations of ions were measured with an ion counter manufactured by Dan Kagaku Co., Ltd., Japan, with the ion sensor portion thereof placed at a distance of 10 cm from the exhaust opening.

As shown in FIG. 26, it was found that, the faster the wind speed of the exhaust air discharged along with ions through the exhaust opening 1b, the higher the ion concentrations, and thus the larger the quantities of ions discharged.

Figure 27:
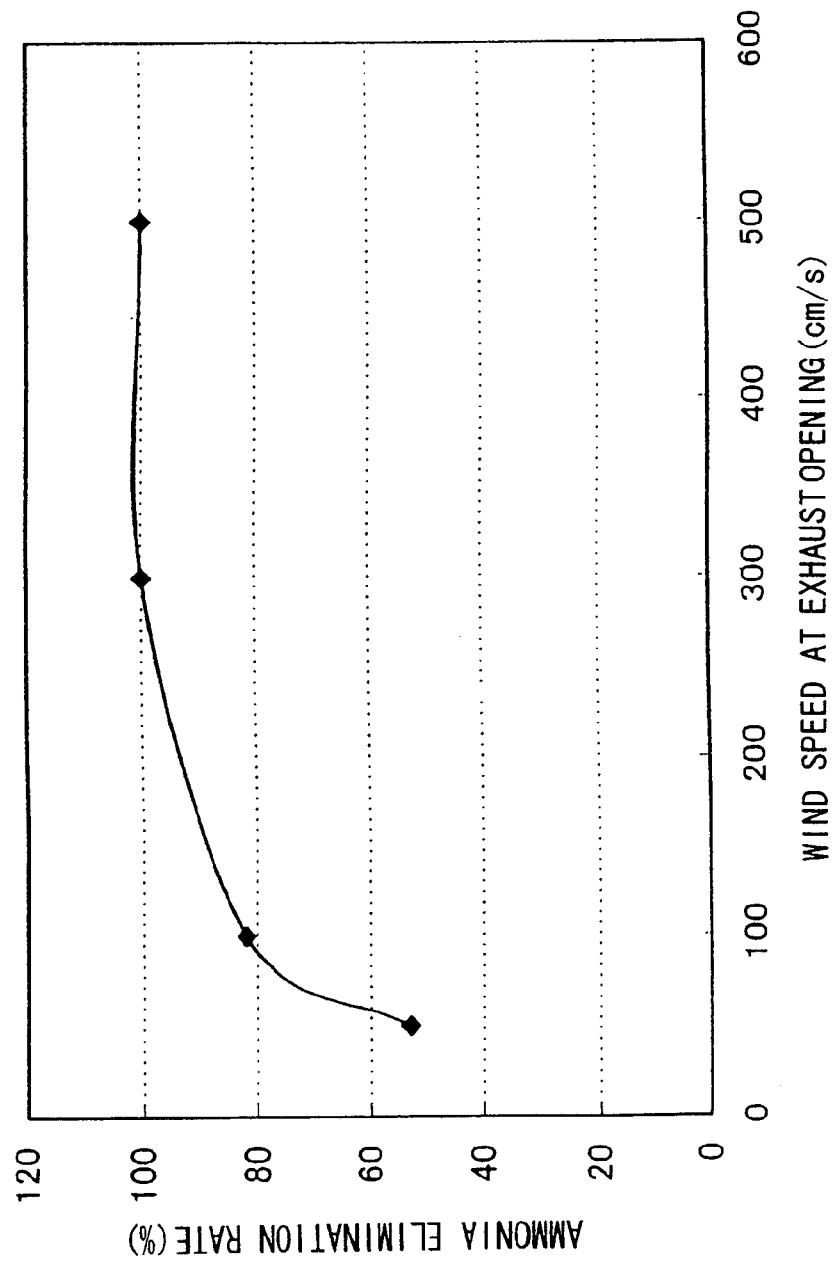
FIG. 27 is a diagram showing the effect of eliminating ammonia achieved by the operation of the electric vacuum cleaner.

Next, it was evaluated how effective the ions discharged from the electric vacuum cleaner were on odor-producing substances. As an odor-producing substance, ammonia was fed into a box of acrylic resin having a volume of 1 $m^3$ in such a way that the initial concentration of ammonia was 10 ppm. Then, the electric vacuum cleaner shown in FIG. 24 was placed inside the box, and the box was then sealed so as to be air-tight. Then, ions were discharged through the exhaust opening at an appropriate wind speed, and, 30 minutes later, the reduced amount of ammonia was measured. Then, on the basis of the initial concentration and the reduced amount of ammonia, the elimination rate was calculated as 100×(reduced amount)/(initial concentration). FIG. 27 shows the result.

As shown in FIG. 27, it was found that, the faster the wind speed, and thus the larger the quantities of ions discharged, the more ammonia was eliminated. It was also found that an ammonia elimination rate of about 50% was achieved when the wind speed of the ion wind blown out through the exhaust opening was 50 cm/s.

On the basis of these facts, it was found that, to satisfactorily eliminate odor-producing substances, the wind speed from the exhaust opening needed to be at least 50 cm/s, which resulted in ion concentrations of about 10,000 ions/$cm^3$.

The electric vacuum cleaner of this embodiment can be realized very simply by externally adding a single device for air purification. This construction can be applied not only to electric vacuum cleaners of the type described above as an example but also to electric vacuum cleaners adopting any other dust collection method.

It is to be understood that the embodiments described above are merely examples of constructions according to the present invention. That is, the present invention can be implemented in any other manners than specifically described above, and many modifications and variations are possible within the scope of the subject matter of the present invention. For example, one of the first, second, third, and eighth embodiments may be combined with one of the fourth, fifth, sixth, seventh, and ninth embodiments.

Specifically, the suction air passage by way of which air is sucked in and discharged may be divided into an upstream part and a downstream part with respect to the electric blower, with an ion generator provided in each of the upstream and downstream parts thereof. This permits not only the interior of the electric vacuum cleaner to be purified, but also permits ions to be mixed with the air discharged out of the electric vacuum cleaner so that purification is performed both inside and outside the electric vacuum cleaner.

The configurations shown in FIGS. 8 to 14, 24, and 25 can be realized very simply by externally adding a device for air purification. The configurations shown in FIGS. 15 to 17, where the ion generator is arranged on the outside, permit easy addition of a separately built ion generator to an existing electric vacuum cleaner.

As shown in FIG. 13, a blower 23a may be additionally provided to discharge ions through the ion discharge port of the ion generator 231. This permits ions to be supplied irrespective of whether the electric blower 14 is being driven or not. Thus, with the electric vacuum cleaner placed in a space, such as a closet, where purification is needed, the ion generator 231 and the blower 231a can be driven to obtain a sterilizing, healing, or other effect that suits the intended purpose.

The ion generator 231 shown in FIGS. 18 to 21 or the ion generator 230 shown in FIG. 13 may be provided in a device of the type that is moved around inside a room as it is used by the user or that has the function of moving around on its own. This makes it possible, as achieved with an electric vacuum cleaner according to the invention, to perform sterilization inside a room to which such a device is carried. Examples of such devices include, to name a few, hair dryers, telephone handsets, intelligent robots, and self-moving cleaners provided with wheels.

Figure 28:
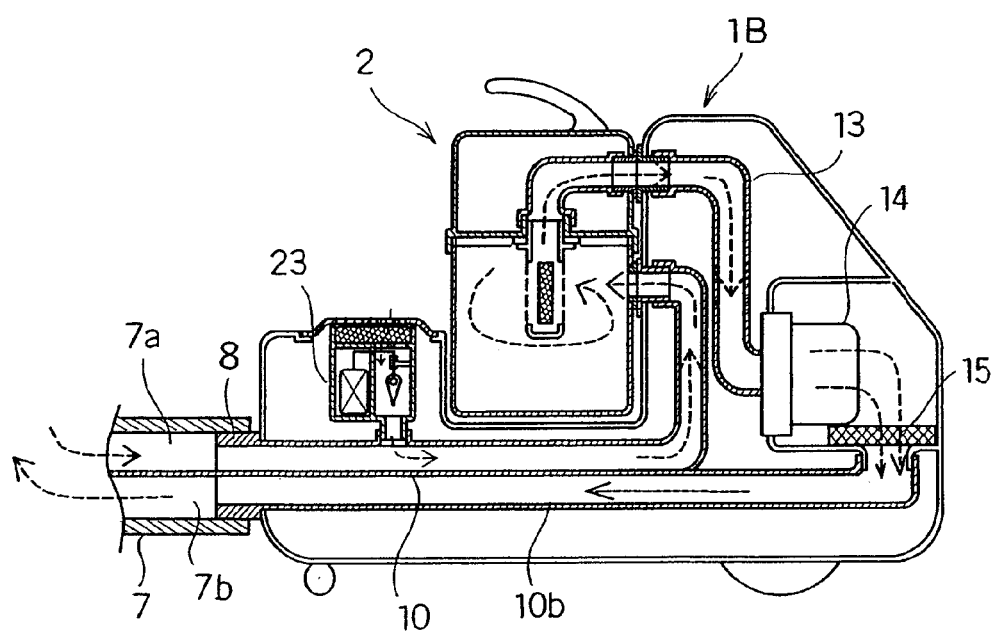
FIG. 28 is a side sectional view showing the internal construction of the body of an example of an exhaust-recycling-type electric vacuum cleaner provided with an ion generator.

Similar effects can be obtained even in a electric vacuum cleaner of the so-called exhaust-recycling type wherein the exhaust is recycled, i.e., the stream of air sucked in is returned from the exhaust side of the electric blower 14 to the nozzle unit 6. FIG. 28 is a sectional view of the body 1B of an exhaust-recycling type electric vacuum cleaner. To the hose socket 8 are connected a first suction air passage 10 that communicates with the dust collecting device and a return stream tube 10b that communicates with the downstream side of the electric blower 14.

Correspondingly, though not illustrated, through a connection pipe and a connection hose are formed a suction air passage 7a and a return stream passage 7b that communicate with the first suction air passage 10 and the return stream pipe 10b, respectively. The connection hose is removably fitted into the hose socket 8. Thus, the suction air passage 7a and the return stream passage 7b communicate with the interior of an unillustrated nozzle unit through the connection hose and the connection pipe.

The stream of air sucked in through the nozzle unit 6 is then sucked, through the suction air passage 7a, first suction air passage 10, dust collection device 2, and second suction air passage 13, into the electric blower 14, and is then recycled by being returned through the deodorizing filter 15, return stream pipe 10b, and return stream passage 7b to the interior of the nozzle unit 6. In this construction, by discharging ions from the ion generator 23 into the suction air passage by way of which air is sucked in through the nozzle unit 6 and fed to the electric blower 14, or into the return stream passage by way of which air is recycled by being returned from the electric blower 14 to the nozzle unit 6, it is possible to purify the suction stream of air or the recycled return stream of air.

INDUSTRIAL APPLICABILITY

As described above, according to the present invention, by discharging both negative and positive ions, or negative ions alone, generated by an ion generator, and by discharging those ions into the air sucked in or into the air discharged out of an electric vacuum cleaner as an electric blower is driven, it is possible to eliminate unpleasant odors produced when the electric vacuum cleaner is used and to kill bacteria such as microorganisms all over a wide area.

In particular, in a case where the ion generator is disposed near an exhaust opening, it is possible to discharge ions into a room. This makes it possible to deliver ions to all corners of the room and purify the air inside the room. Moreover, by driving the ion generator along with a blowing means for blowing ions, it is possible to purify the air in the room even while the electric vacuum cleaner is stored.

Moreover, the ion generator uses a needle-shaped electrode. This permits an electric field to concentrate, and thus permits discharge to take place more easily, resulting in efficient discharge of ions into the sucked air. In addition, this needle-shaped electrode is arranged along the stream of air. This makes the electrode almost free from dust electrostatically settling thereon, and thus makes its maintenance easy.

Moreover, the present invention can be applied to electric vacuum cleaners adopting any dust collection method, such as those employing a cyclone-type dust collecting device or a dust collection bag. Thus, simply by adding an ion generator as a device for air purification, it is possible to purify air that tends to be polluted during cleaning.

The invention claimed is:

1. An electric vacuum cleaner that, while driving an electric blower, sucks in air containing dust through a suction portion, then passes the air through a suction air passage, and then discharges the air out of the electric vacuum cleaner through an exhaust port, wherein
    the suction air passage comprises a first suction air passage communicating with the suction port and a second suction air passage communicating with the exhaust port,
    a dust collector is provided within a body of the electric vacuum cleaner and between the first and second suction air passages,
    an ion generator is provided in the first suction air passage within the body of the electric vacuum cleaner, and
    ions generated from the ion generator along a direction in which air flows are mixed with the air and fed through the first suction air passage into the dust collector.

2. The electric vacuum cleaner according to claim 1, wherein
    the ion generator generates $H^+(H_2O)_n$ as positive ions and $O_2^-(H_2O)_m$ as negative ions by applying positive and negative voltages to electrodes, and
    the positive and negative ions are mixed to air inside the first suction air passage so that airborne germs present in the air are killed by hydroxyl radical .OH and hydrogen peroxide $H_2O_2$, which are active species generated through reaction between the positive and negative ions.

3. The electric vacuum cleaner according to claim 1, wherein the ions generated by the ion generator are fed into the first suction air passage by suction resulting from the electric blower being driven.

4. The electric vacuum cleaner according to claim 1, wherein the ion generator comprises two electrodes, and generates the positive and negative ions from different electrodes.

5. The electric vacuum cleaner according to claim 1, wherein the negative ions are generated in an amount equal to or greater than an amount in which the positive ions are generated.

6. The electric vacuum cleaner according to claim 1, wherein the dust collector is removably attached to a body of the electric vacuum cleaner and, with the dust collector attached, the air containing dust sucked in through the suction portion passes through the dust collector and is then discharged through the exhaust port.

7. An electric vacuum cleaner that, while driving an electric blower, sucks in air containing dust through a suction portion, then passes the air through a suction air passage, and then discharges the air out of the electric vacuum cleaner through an exhaust port, wherein
    the suction air passage comprises a first suction air passage communicating with the suction port and a second suction air passage communicating with the exhaust port,
    a dust collector is provided within a body of the electric vacuum cleaner and between the first and second suction air passages, an ion generator is provided in the dust collector, and ions generated from the ion generator along a direction in which air flows are mixed with the air and fed into the dust collector.

8. The electric vacuum cleaner according to claim 7, wherein the ion generator generates $H^+(H_2O)_n$ as positive ions and $O_2^-(H_2O)_m$ as negative ions by applying positive and negative voltages to electrodes, and the positive and negative ions are mixed to air inside the first suction air passage so that airborne germs present in the air are killed by hydroxyl radical .OH and hydrogen peroxide $H_2O_2$, which are active species generated through reaction between the positive and negative ions.

9. The electric vacuum cleaner according to claim 7, wherein the ion generator comprises two electrodes, and generates the positive and negative ions from different electrodes.

10. The electric vacuum cleaner according to claim 7, wherein the negative ions are generated in an amount equal to or greater than an amount in which the positive ions are generated.

11. The electric vacuum cleaner according to claim 7, wherein the dust collector is removably attached to a body of the electric vacuum cleaner and, with the dust collector attached, the air containing dust sucked in through the suction portion passes through the dust collector and is then discharged through the exhaust port.

* * * * *